(12) United States Patent
Rodgers et al.

(10) Patent No.: US 7,987,069 B2
(45) Date of Patent: Jul. 26, 2011

(54) MONITORING PATIENT SUPPORT EXITING AND INITIATING RESPONSE

(75) Inventors: Mark E. Rodgers, Jackson, MS (US); Douglas E. Parsell, Ridgeland, MS (US)

(73) Assignee: Bee Cave, LLC, Austin, TX (US)

( * ) Notice: Subject to any disclaimer, the term of this patent is extended or adjusted under 35 U.S.C. 154(b) by 388 days.

(21) Appl. No.: 12/268,728

(22) Filed: Nov. 11, 2008

(65) Prior Publication Data

US 2009/0119843 A1    May 14, 2009

Related U.S. Application Data

(63) Continuation-in-part of application No. 12/101,602, filed on Apr. 11, 2008.

(60) Provisional application No. 60/987,137, filed on Nov. 12, 2007.

(51) Int. Cl.
    *G01C 9/06* (2006.01)
(52) U.S. Cl. ........................ 702/150; 770/151; 340/573.1
(58) Field of Classification Search ............... 5/611, 613, 5/600, 616–618; 702/150–151; 347/573.1
    See application file for complete search history.

(56) References Cited

U.S. PATENT DOCUMENTS

| | | |
|---|---|---|
| 1,388,242 A | 8/1921 | Dodds |
| 2,592,166 A | 4/1952 | McLean et al. |
| 2,604,639 A | 7/1952 | Killifer |
| 3,039,118 A | 6/1962 | Hutt |
| 3,919,727 A | 11/1975 | Paine |
| 3,972,320 A | 8/1976 | Kalman |
| 4,057,240 A | 11/1977 | Damico et al. |
| 4,087,872 A | 5/1978 | Smirle |
| 4,152,795 A | 5/1979 | Rodosta et al. |
| 4,196,425 A | 4/1980 | Williams, Jr. et al. |
| 4,539,560 A | 9/1985 | Fleck et al. |
| 4,633,237 A | 12/1986 | Tucknott et al. |
| 4,814,751 A | 3/1989 | Hawkins et al. |
| 4,837,877 A | 6/1989 | Hamada et al. |

(Continued)

FOREIGN PATENT DOCUMENTS

DE    3443334    6/1986

(Continued)

OTHER PUBLICATIONS

Notice of Allowance dated Mar. 8, 2010 cited in U.S. Appl. No. 11/608,125.

(Continued)

*Primary Examiner* — Fredrick Conley
(74) *Attorney, Agent, or Firm* — Workman Nydegger

(57) ABSTRACT

The present invention relates to systems and methods for monitoring patient support exiting and initiating a response. Movement data is accessed from sensors (e.g., cameras) that are monitoring a patient resting on a support platform. A motion capture pattern summary is generated from the accessed movement data. The motion capture pattern summary is compared to one or more movement pattern data sets in a library of movement pattern data sets. It is determined that the motion capture pattern summary is sufficiently similar to one of the one or more movement pattern data sets in the library of movement pattern data sets. From the determined similarity it is determined that the patient is attempting to exit the support platform. Remedial measures are initiated to prevent the detected platform support exiting attempt.

30 Claims, 18 Drawing Sheets

U.S. PATENT DOCUMENTS

| | | | |
|---|---|---|---|
| 4,907,845 A | 3/1990 | Wood |
| 4,947,152 A | 8/1990 | Hodges |
| 4,952,928 A | 8/1990 | Carroll et al. |
| 5,008,654 A | 4/1991 | Callaway |
| 5,095,560 A | 3/1992 | Volker |
| 5,107,845 A | 4/1992 | Guern et al. |
| 5,218,344 A | 6/1993 | Ricketts |
| 5,276,432 A | 1/1994 | Travis |
| 5,353,012 A | 10/1994 | Barham et al. |
| 5,365,217 A | 11/1994 | Toner |
| 5,416,695 A | 5/1995 | Stutman et al. |
| 5,490,298 A | 2/1996 | Goldsmith et al. |
| 5,495,288 A | 2/1996 | Broady et al. |
| 5,519,380 A | 5/1996 | Edwards |
| 5,583,758 A | 12/1996 | McIlroy et al. |
| 5,633,627 A | 5/1997 | Newham |
| 5,650,770 A | 7/1997 | Schlager et al. |
| 5,714,931 A | 2/1998 | Petite et al. |
| 5,732,401 A | 3/1998 | Conway |
| 5,738,102 A | 4/1998 | Lemelson |
| 5,740,800 A | 4/1998 | Hendrickson et al. |
| 5,765,139 A | 6/1998 | Bondy |
| 5,780,798 A | 7/1998 | Hall-Jackson |
| 5,781,442 A | 7/1998 | Engleson et al. |
| 5,831,669 A | 11/1998 | Adrain |
| 5,844,488 A | 12/1998 | Musick |
| 5,877,675 A | 3/1999 | Rebstock et al. |
| 5,941,836 A | 8/1999 | Friedman |
| 5,946,659 A | 8/1999 | Lancelot et al. |
| 5,953,704 A | 9/1999 | McIlroy et al. |
| 6,049,281 A | 4/2000 | Osterweil |
| 6,067,019 A | 5/2000 | Scott |
| 6,078,261 A | 6/2000 | Davsko |
| 6,104,295 A | 8/2000 | Gaisser et al. |
| 6,125,350 A | 9/2000 | Dirbas |
| 6,154,139 A | 11/2000 | Heller |
| 6,160,478 A | 12/2000 | Jacobson et al. |
| 6,169,484 B1 | 1/2001 | Schuchman et al. |
| 6,204,767 B1 | 3/2001 | Sparks |
| 6,259,355 B1 | 7/2001 | Chaco et al. |
| 6,402,691 B1 | 6/2002 | Peddicord et al. |
| 6,433,690 B2 | 8/2002 | Petelenz et al. |
| 6,466,125 B1 | 10/2002 | Richards et al. |
| 6,524,239 B1 | 2/2003 | Reed et al. |
| 6,583,727 B2 | 6/2003 | Nunome |
| 6,611,206 B2 | 8/2003 | Eshelman et al. |
| 6,611,783 B2 * | 8/2003 | Kelly et al. ............... 702/150 |
| 6,624,754 B1 | 9/2003 | Hoffman et al. |
| 6,640,212 B1 | 10/2003 | Rosse |
| 6,674,403 B2 | 1/2004 | Gray et al. |
| 6,748,250 B1 | 6/2004 | Berman et al. |
| 6,753,783 B2 | 6/2004 | Friedman et al. |
| 6,788,206 B1 | 9/2004 | Edwards |
| 6,791,460 B2 | 9/2004 | Dixon et al. |
| 6,804,656 B1 | 10/2004 | Rosenfeld et al. |
| 6,821,258 B2 | 11/2004 | Reed et al. |
| 6,822,571 B2 | 11/2004 | Conway |
| 6,830,180 B2 | 12/2004 | Walsh |
| 6,838,992 B2 | 1/2005 | Tenarvitz |
| 6,876,303 B2 | 4/2005 | Reeder et al. |
| 6,897,781 B2 | 5/2005 | Cooper et al. |
| 6,900,732 B2 | 5/2005 | Richards |
| 6,909,367 B1 | 6/2005 | Wetmore |
| 6,915,170 B2 | 7/2005 | Engleson et al. |
| 6,941,239 B2 | 9/2005 | Unuma et al. |
| 6,958,706 B2 | 10/2005 | Chaco et al. |
| 6,968,294 B2 | 11/2005 | Gutta et al. |
| 6,975,230 B1 | 12/2005 | Brilman |
| 6,987,232 B2 | 1/2006 | Smith et al. |
| 7,001,334 B2 | 2/2006 | Reed et al. |
| 7,035,432 B2 | 4/2006 | Szuba |
| 7,110,569 B2 | 9/2006 | Brodsky et al. |
| 7,198,320 B2 | 4/2007 | Rasmussen |
| 7,242,306 B2 | 7/2007 | Wildman et al. |
| 7,369,680 B2 | 5/2008 | Trajkovic et al. |
| 7,406,731 B2 * | 8/2008 | Menkedick et al. ............... 5/618 |
| 7,452,336 B2 | 11/2008 | Thompson |
| 7,502,498 B2 | 3/2009 | Wen et al. |
| 7,505,620 B2 | 3/2009 | Braune et al. |
| 2001/0044965 A1 | 11/2001 | Blevins |
| 2002/0046423 A1 | 4/2002 | Vilsmeier |
| 2002/0140559 A1 | 10/2002 | Zhou et al. |
| 2002/0165733 A1 | 11/2002 | Pulkkinen et al. |
| 2003/0013459 A1 | 1/2003 | Rankin et al. |
| 2003/0028399 A1 | 2/2003 | Davis et al. |
| 2003/0058111 A1 | 3/2003 | Lee et al. |
| 2003/0069815 A1 | 4/2003 | Eisenberg et al. |
| 2003/0167187 A1 | 9/2003 | Bua |
| 2003/0169171 A1 | 9/2003 | Strubbe et al. |
| 2004/0172290 A1 | 9/2004 | Leven et al. |
| 2004/0193449 A1 | 9/2004 | Wildman et al. |
| 2005/0125899 A1 | 6/2005 | Hanson et al. |
| 2005/0190062 A1 | 9/2005 | Sullivan et al. |
| 2005/0240086 A1 | 10/2005 | Akay |
| 2005/0242946 A1 | 11/2005 | Hubbard et al. |
| 2005/0283382 A1 | 12/2005 | Donoghue et al. |
| 2006/0033625 A1 | 2/2006 | Johnson et al. |
| 2006/0053035 A1 | 3/2006 | Eisenberg |
| 2006/0056655 A1 | 3/2006 | Wen et al. |
| 2006/0265805 A1 | 11/2006 | Bellingroth |
| 2007/0033072 A1 | 2/2007 | Bildirici |
| 2007/0132597 A1 | 6/2007 | Rodgers |
| 2007/0157385 A1 | 7/2007 | Lemire et al. |
| 2007/0222599 A1 | 9/2007 | Coveley et al. |
| 2008/0272918 A1 * | 11/2008 | Ingersoll ............... 340/573.1 |

FOREIGN PATENT DOCUMENTS

| | | |
|---|---|---|
| EP | 141881 | 5/1985 |
| JP | 07/334579 | 12/1995 |
| JP | 2004016749 | 1/2004 |
| JP | 04/078344 | 3/2004 |
| JP | 06/092147 | 4/2006 |
| WO | WO 9527467 | 10/1995 |
| WO | WO 2006/011124 | 2/2006 |
| WO | WO 2006/117788 | 5/2006 |

OTHER PUBLICATIONS

Office Action dated Mar. 19, 2010 cited in U.S. Appl. No. 11/608,074.
Final Office Action dated Aug. 5, 2009 cited in U.S. Appl. No. 11/779,182.
Office Action dated Aug. 6, 2009 cited in U.S. Appl. No. 11/779,096.
Final Office Action dated Aug. 20, 2009 cited in U.S. Appl. No. 11/608,125.
Final Office Action dated Aug. 17, 2009 cited in U.S. Appl. No. 11/608,074.
Office Action dated Apr. 13, 2010 cited in U.S. Appl. No. 11/774,471.
Office Action dated May 12, 2010 cited in U.S. Appl. No. 11/561,263.
Office Action dated Jul. 8, 2010 cited in U.S. Appl. No. 11/779,096.
Office Action dated Jul. 7, 2010 cited in U.S. Appl. No. 11/779,182.
Notice of Allowance dated Apr. 29, 2010 cited in U.S. Appl. No. 11/608,074.
U.S. Appl. No. 12/001,675, filed Dec. 11, 2007, Parsell.
Final Office Action dated Apr. 28, 2009 cited in U.S. Appl. No. 11/774,471.
Chang, et al., Pervasive Observation Medicine: The Application of RFID to Improve Patent Safety in Observation Unit of Hospital Emergency Department, 2005.
Exavera Technologies, Identifying . . . the Future of Healthcare, 2006.
Ho, et al., A Prototype on RFID and Sensore Networks for Elder Healthcare: Progress Report, SIGCOMM '05 Workshops, Aug. 2005.
Sangwan, et al., Using RFID Tags for Tracking Patients, Charts, and Medical Equipment Within an Integrated Health Delivery Network, 2005.
VersusTech, Oct. 23, 2005, pp. 1-8.
U.S. Appl. No. 11/608,074, mail date Mar. 18, 2009, Non-Final OA.
U.S. Appl. No. 11/608,125, mail date Jan. 9, 2009, Non-Final OA.
U.S. Appl. No. 11/774,471, mail date Dec. 23, 2008, Non-Final OA.
U.S. Appl. No. 11/779,096, mail date Mar. 18, 2009, Non-Final OA.
U.S. Appl. No. 11/779,182, mail date Jan. 26, 2009, Non-Final OA.
Office Action dated Sep. 15, 2009 cited in U.S. Appl. No. 11/774,471.
Office Action dated Oct. 28, 2009 cited in U.S. Appl. No. 11/561,263.

* cited by examiner

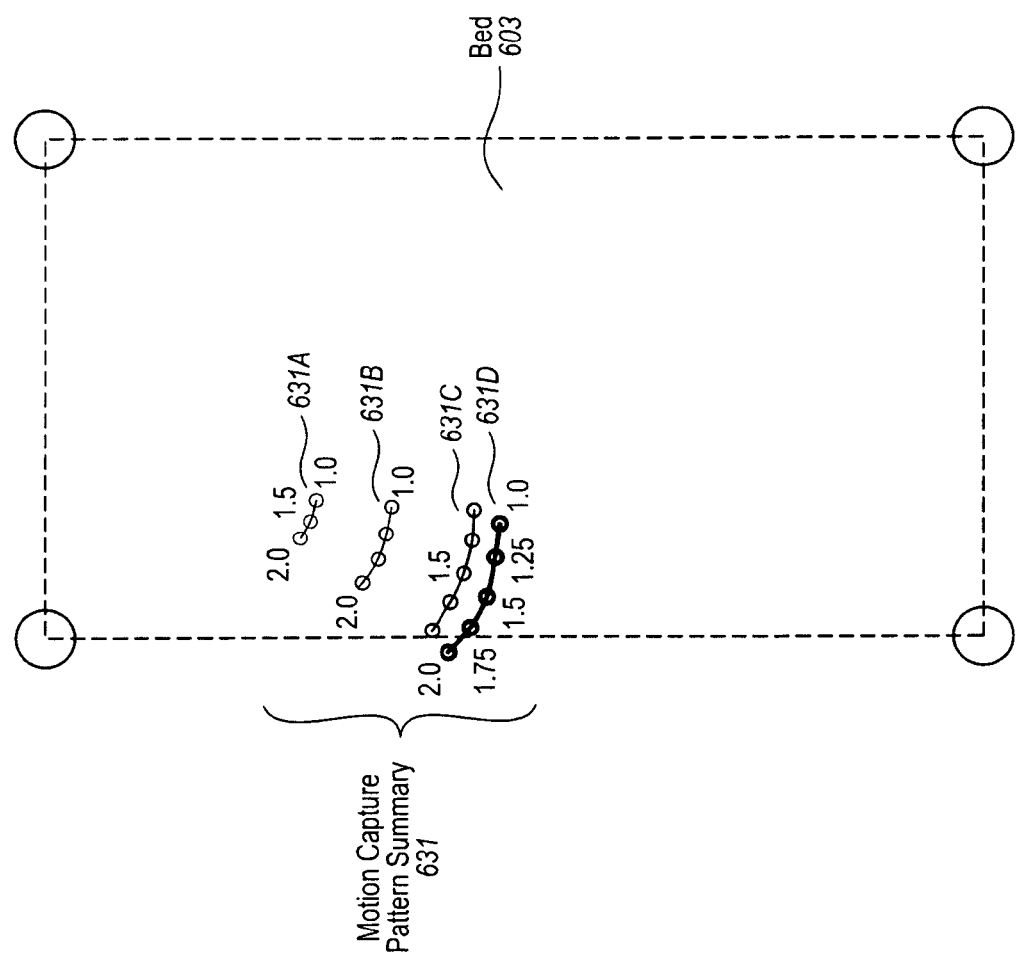

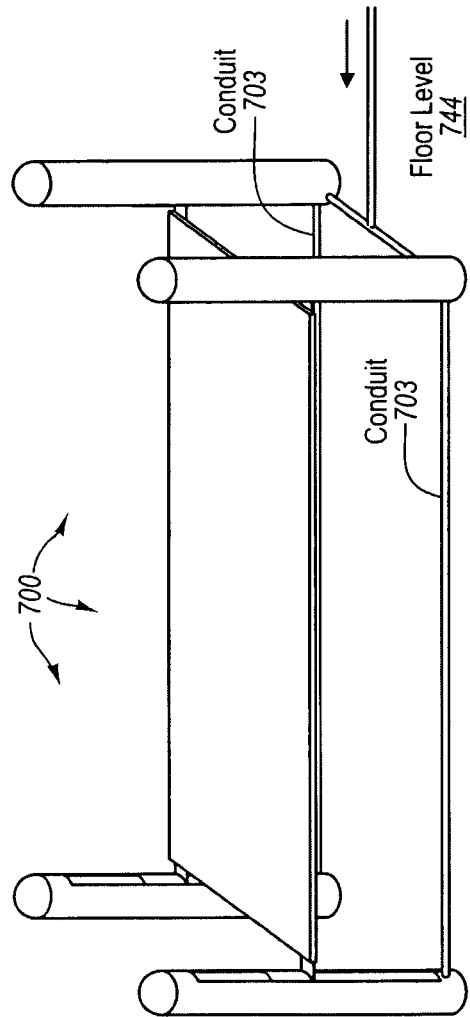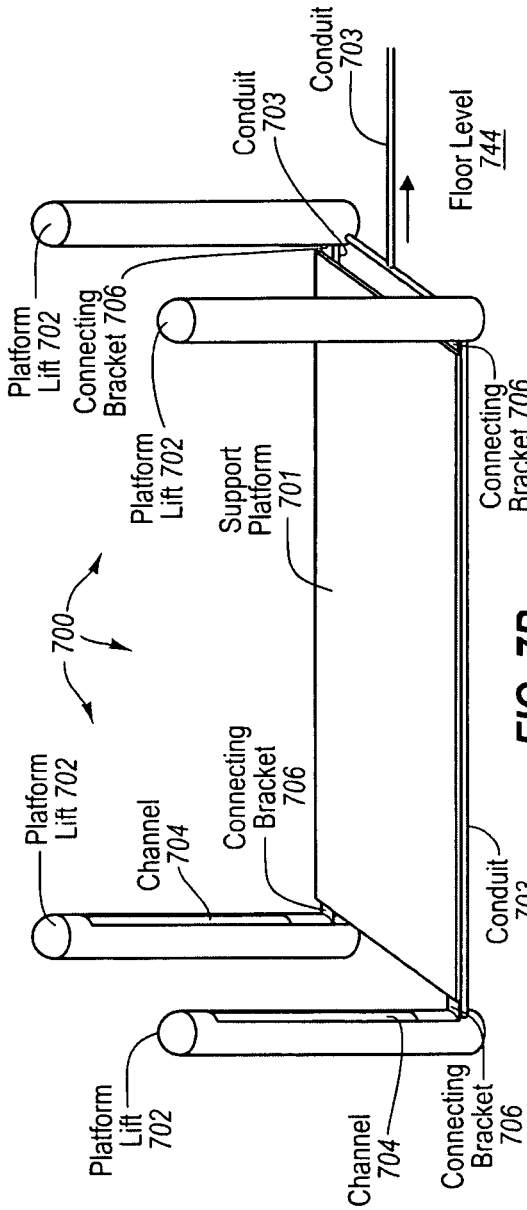
FIG. 7A
(Raised Configuration)
FIG. 7B
(Lowered Configuration)

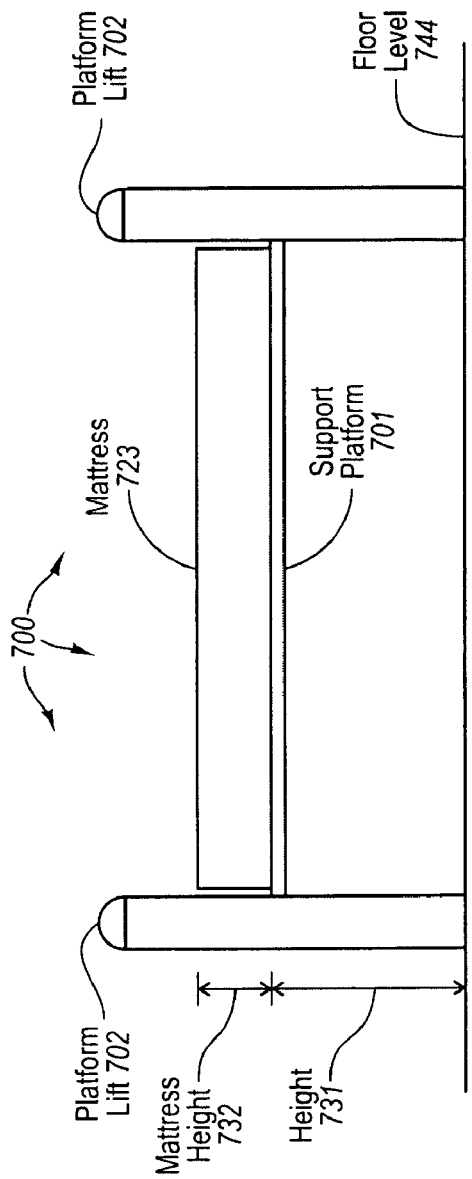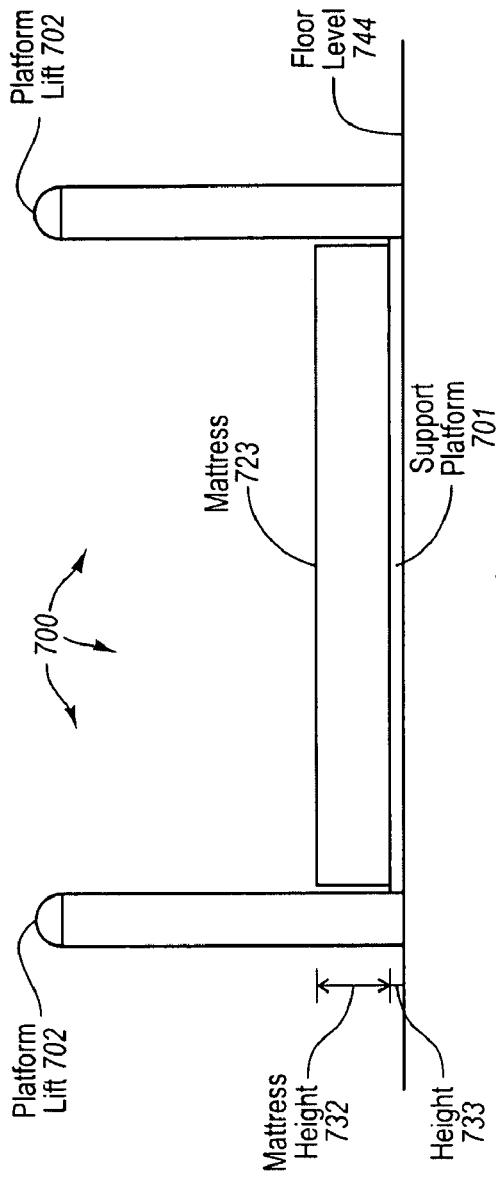

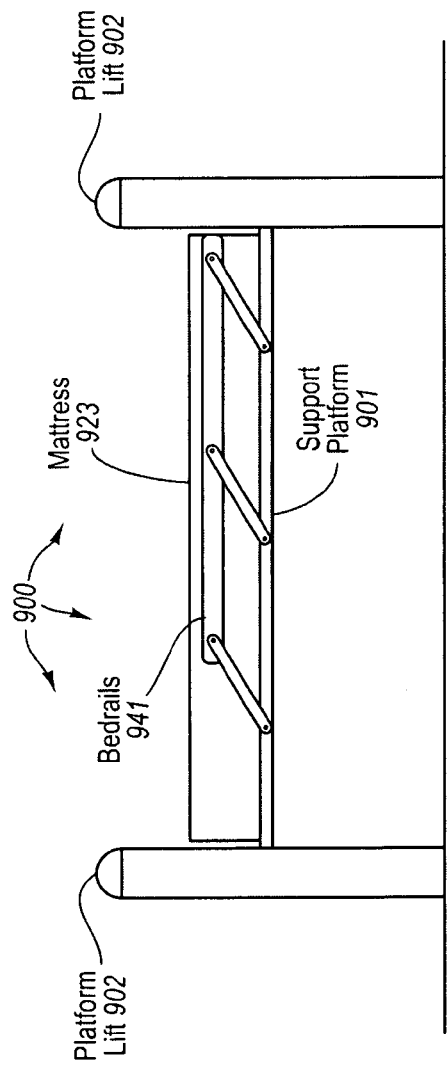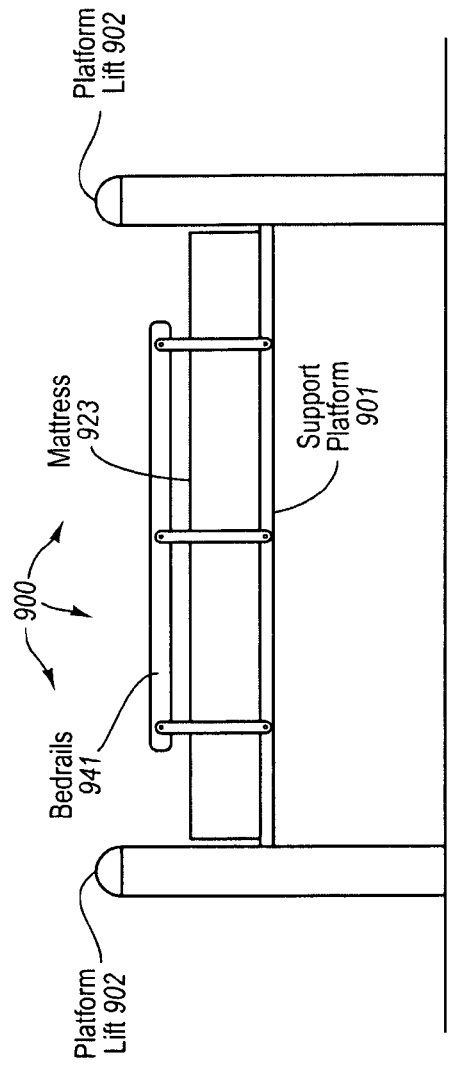
FIG. 9A
FIG. 9B

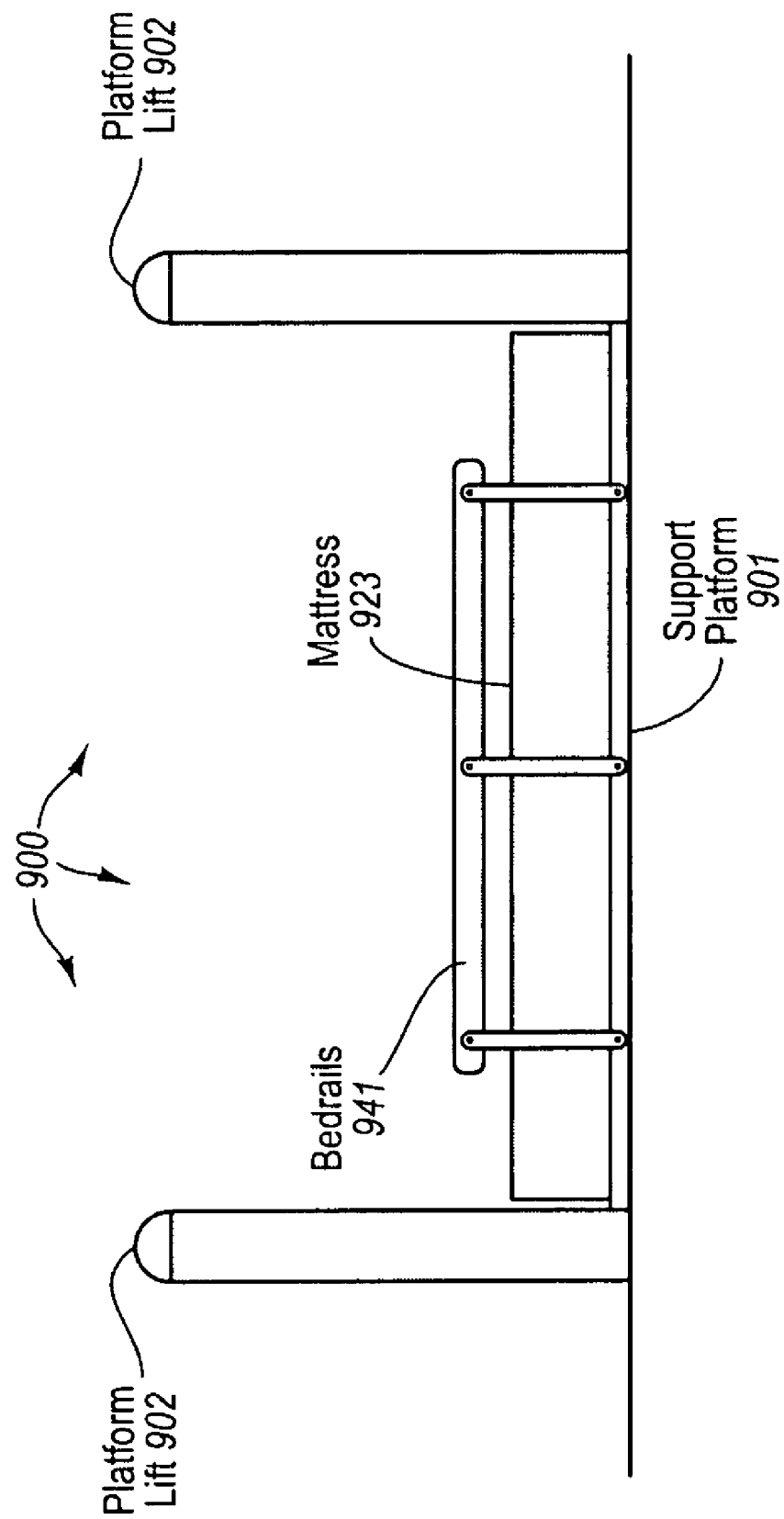

MONITORING PATIENT SUPPORT EXITING AND INITIATING RESPONSE

CROSS-REFERENCE TO RELATED APPLICATIONS

This application is a continuation-in-part of U.S. patent application Ser. No. 12/101,602 entitled "Automatically Adjusting Patient Platform Support Height In Response To Patient Related Events," filed Apr. 11, 2008. This application claims the benefit of U.S. Provisional Application No. 60/987,137, entitled "Methods And Systems For Monitoring Patient Support Exiting And Initiating Response," filed on Nov. 12, 2007. The disclosures of the foregoing applications are incorporated herein in their entirety

BACKGROUND

1. Background and Relevant Art

Healthcare facilities provide clinical and/or wellness health care for patients and/or residents (hereinafter collectively referred to as "patients") residing at such facilities. Hospitals and medical clinics provide clinical health care. Assisted living and nursing homes focus primarily on wellness health care.

One area of critical concern is preventing or reducing the incidence of patient falls, which can occur in a variety of circumstance but which commonly result from unauthorized or unassisted bed exiting, wheelchair exiting, and wheelchair to bed transfer. Falls often occur due to the inability of health care facilities to provide continuous, direct supervision of patients.

Most facilities provide at least some physical monitoring and supervision of patients to ensure they are protected from physical injury. Many facilities include a central station (e.g., a nurse station) that functions as a primary gathering and dispatch location for caregivers. From time to time, at specified intervals, or in response to a patient or resident request, a caregiver can move from the central station to a patient's location (e.g., room) and monitor or provide appropriate care. In many cases it may not be feasible to provide round the clock supervision of every patient due to financial and/or logistical restraints. However, without continuous direct supervision there is often no way for a health care provider to know when a particular patient may be engaging in behavior which places them at a high risk for a fall.

Some healthcare facilitates attempt to supplement physical monitoring and supervision with automated patient monitoring systems. Various different monitoring mechanisms have been used to detect movements and/or positions of a patient indicative of subsequent bed exiting. One example of an automated patient monitoring system is fixing an electric eye or camera on a location near where a patient is lying. An alarm might sound if a line or plane is broken by the patient. Another example involves devices that detect patient motion. Yet another proposes comparing successive images of a patient to determine patient acceleration and relative location. One particularly creative patient monitoring system claims to be able to monitor and interpret a wide variety of patient movements, including patient falls, by taking and analyzing 3-dimensional images of a patient.

However, most, if not all, of these automated patient monitoring systems lack feasibility and have not been implemented on a wide scale. A problem with many proposed systems is they only crudely predict or determine actual patient bed exiting or other potentially dangerous movements. The result is a high level of false positives and false negatives. Repeated false positives might cause overworked caregivers to ignore true positives. False negatives provide no early warning of patient falls.

A common problem that leads to high levels of false positives and false negatives is a "one size fits all" approach to detecting patient movements. Although people often have uniquely personal ways of getting out of bed, no attempt is made in conventional monitoring systems to understand the idiosyncratic movements and habits of a particular patient. For example, one patient might typically grasp the left handrail when commencing to bed exit while another might slide towards the foot of the bed. Persons who are left handed might exit their beds oppositely from right handed persons. Certain medical conditions might determine or alter bed exiting behavior (e.g., a person with an incision might protect against harm or pain by avoiding movements that would apply stress to the incision, even if such movements were previously used to bed exit when the patient was healthy).

Further, even when a potential bed exiting event is detected, physical intervention is typically required to mitigate possible injury from an actual bed exit attempt. Far too often, the time required to alert staff and produce a physical presence within the patient's room exceeds the time required for the patient to attempt a bed exit. Non-physical intervention methods, such as, for example, audio and/or video counseling, can extend the window of opportunity for intervention, but an unattended bed exit attempt can still occur.

BRIEF SUMMARY OF THE INVENTION

The present invention relates to systems and methods for monitoring patient support exiting and initiating response. A computer system accesses movement data from sensors that are monitoring a patient resting on a support platform. The movement data is indicative of movement in one or more portions of the patient's body. The computer system generates a motion capture pattern summary for the patient from the accessed movement data. The motion capture pattern summary captures movements for the one or more portions of the patient's body. The computer system compares the motion capture pattern summary to one or more movement pattern data sets in a library of movement pattern data sets. Movement pattern data sets in the library of movement pattern data sets are representative of movements having some probability of indicating platform support exiting.

The computer system determines that the motion capture pattern summary is sufficiently similar to one of the one or more movement pattern data sets in the library of movement pattern data sets. The computer system detects that the patient is attempting to exit the support platform based on the determined similarity. The computer system initiates remedial actions, such as, for example, lowering the support platform, raising bedrails, and notifying caregivers, in response to detecting the attempt to exit the support platform.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 6B illustrates a motion capture pattern summary for the patient depicted in FIG. 6A.

FIG. 7A illustrates an example of a height adjusting bed in a raised configuration.

FIG. 7B illustrates an example of a height adjusting bed in a lowered configuration.

FIG. 7E illustrates an example of a height adjusting bed including a mattress in a raised configuration.

FIG. 7F illustrates an example of a height adjusting bed including a mattress in a lowered configuration.

FIG. 9A illustrates an example of a bed in a raised configuration with bed rails in a lowered configuration.

FIG. 9B illustrates an example of a bed in a raised configuration with bed rails in a raised configuration.

FIG. 9C illustrates an example of a bed in a lowered configuration with bed rails in a raised configuration.

DETAILED DESCRIPTION

Embodiments of the present invention extend to systems, methods, and computer program products for monitoring patient support exiting and initiating response. A computer system accesses movement data from sensors that are monitoring a patient resting on a support platform. The movement data is indicative of movement in one or more portions of the patient's body. The computer system generates a motion capture pattern summary for the patient from the accessed movement data. The motion capture pattern summary captures movements for the one or more portions of the patient's body. The computer system compares the motion capture pattern summary to one or more movement pattern data sets in a library of movement pattern data sets. Movement pattern data sets in the library of movement pattern data sets are representative of movements having some probability of indicating platform support exiting.

The computer system determines that the motion capture pattern summary is sufficiently similar to one of the one or more movement pattern data sets in the library of movement pattern data sets. The computer system detects that the patient is attempting to exit the support platform based on the determined similarity. The computer system initiates remedial actions, such as, for example, lowering the support platform, raising bedrails, and notifying caregivers, in response to detecting the attempt to exit the support platform.

The term "support platform" shall be broadly understood to include any platform that is configured to at least partially support a patient's weight above-floor level or some other surface such that the patient is relieved from having to fully support their own body weight. Support platform is defined to include beds, wheelchairs, gurneys, couches, chairs, recliners, and toilets.

The term "patient fall" shall be broadly understood to include falling to the ground or floor, falling into stationary or moving objects, falling back onto a support, or any other falling motion caused at least in part by gravity that may potentially cause physical injury and/or mental or emotional trauma.

The terms "rest" and "resting" as it relates to a patient resting on a support shall be broadly understood as any situation where the support provides at least some counter action to the force of gravity. Thus, a patient may "rest" on a support while lying still, sitting up, moving, lying down, or otherwise positioned relative to the support so long as the support acts in some way to separate a patient from the floor or surface upon which the support is itself positioned.

Operating Environment for Detecting and Responding to Support Exiting

Figure 1:
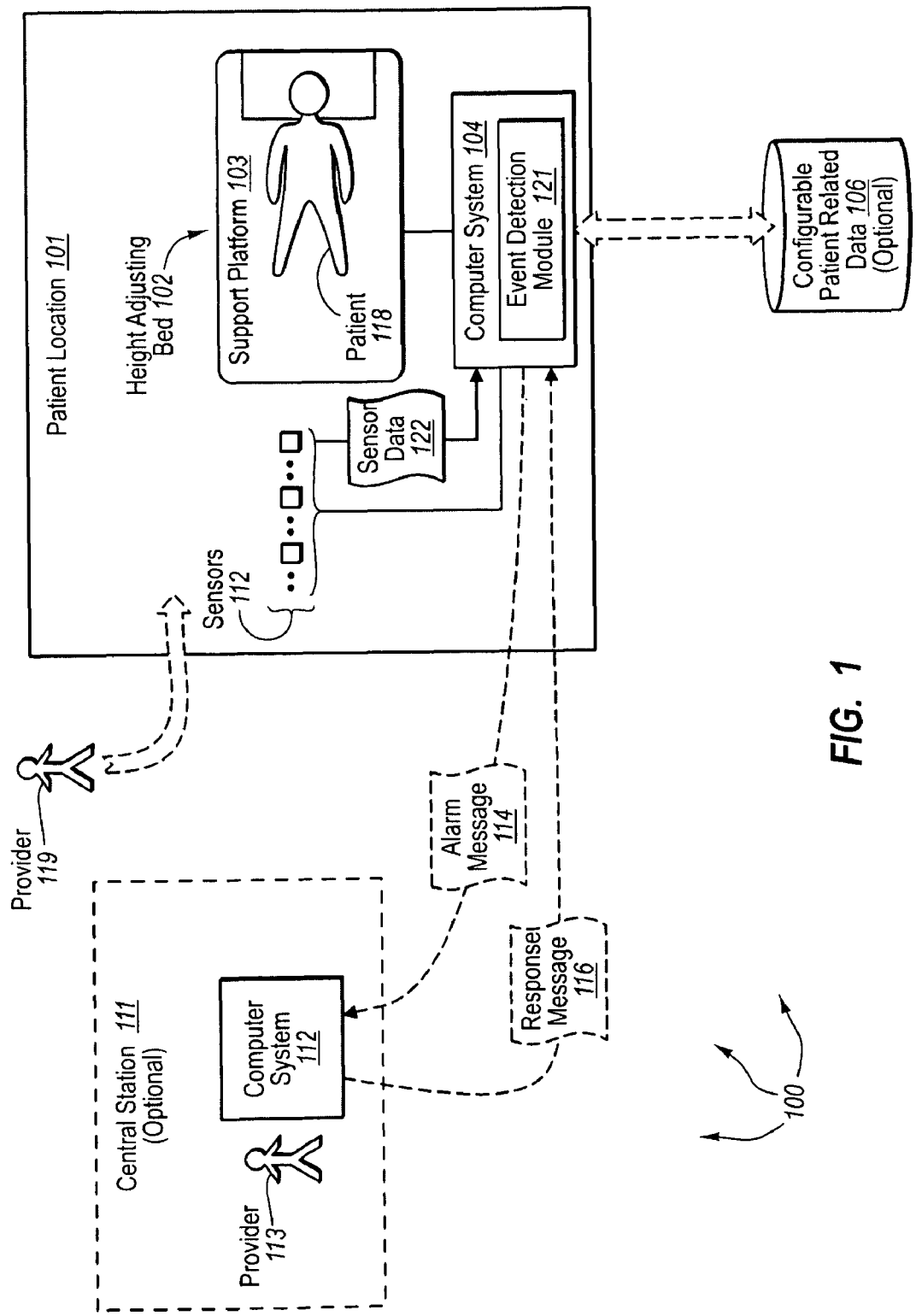
FIG. 1 illustrates an example operating environment for automatically detecting and responding to support exiting events.

FIG. 1 illustrates operating environment 100 for automatically adjusting patient support platform height in response to patient related events. Operating environment 100 includes patient location 101. Patient location 101 can be a room in a healthcare facility, in a patient's house, etc. Patient location 101 may or may not be monitored by other individuals, such as, for example, health care providers. Further, even when patient location 101 is monitored, the level and/or type of monitoring can vary. For example, patient location 101 can have a real-time video feed to a mentoring location. On the other, hand patient location can be physical checked at various time intervals by a provider. Patient location 101 includes height adjusting bed 102, sensors 112, and computer system 101.

Height adjusting bed 102 includes support platform 103. As depicted, patient 118 is resting on support platform 103. Height adjusting bed 102 can also include any of a number of mechanisms (described below in further detail) for adjusting the height of support platform 103 in a relatively quick and controlled manner. For example, the height of a patient support platform 103 can be lowered at least closer (and essentially all the way) to floor level to reduce fall distances of patient 118.

Sensors 112 can include various types of sensors, such as, for example, video cameras, still cameras, microphones, pressure sensors, acoustic sensors, temperature sensors, heart rate monitors, conductivity sensors, global positioning sensors ("GPS"), manual assistance switches/buttons, bed sensors, handrail sensors, mattress sensors, location sensors, oxygen tank sensors, etc. Sensors 112 can include transmitters and receivers that utilize any of a variety of different frequency ranges in the electromagnetic spectrum. For example, sensors 112 can include transmitters and receivers that utilize one or more of: Infrared, visible light, Ultraviolet, Microwave, Radio Frequency, etc. signals. Sensors 112 can also include transmitters and receivers that utilize any of a variety of different frequency ranges of vibrational mechanical energy (cyclic sound pressure). For example, sensors 112 can include transmitters and receivers that utilize one or more of: infrasound (less than approximately 20 Hz), human perceivable sound (approximately 20 Hz to 20 KHz), and ultrasound (greater than approximately 20 KHz) signals.

Combinations of different types and/or numbers of sensors 112 can be used to detect patient related events, such as, for example, platform support (bed) exiting. Each of sensors 112 can output sensor data that is accessible to computer system 104. Computer system 104 includes event detection module 121. Event detection module 121 is generally configured to monitor and process sensor data from sensors 112. Based on monitored and/or processed sensor data, event detection module 121 can detect when a combination sensor data indicates the occurrence of a potentially actionable event. For example, event detection module 121 can monitor and can process sensor data 122 to detect potentially actionable events (e.g., at attempt to exit support platform 103) for patient 118.

In some embodiments, event detection module 121 also considers other unique patient related data when determining that a potentially actionable event has occurred. For example, event detection module 121 can refer to configurable patient related data 106, such as, for example, a unique patient profile for patient 118, when determining that a potentially actionable event has occurred. Among other types of data, unique patient related data can contain data relating to support exiting behavior of a patient. Accordingly, configurable patient related data 106 can contain data relating to the support exiting behavior of a patient 118. Thus when appropriate, event detection module 121 can monitor and process sensor data 122 in combination with configurable patient related data 106 to detect potentially actionable events (e.g., an attempt to exit support platform 103) for patient 118.

In response to a detected event, computer system 104 can implement one or more automated actions for a patient's benefit. For example, in response to detecting that patient 118 is attempting to exit support platform 103, computer system 104 can activate a height adjustment mechanism of height adjusting bed 102 to lower support platform 103 to a lower height. Accordingly, the fall distance of patient 118 is reduced to lessen the possibility of injury from a fall.

In some embodiments, such as, for example, at a healthcare facility, patient location 101 is monitored from central station 111. Central location 111 includes computer system 112. Computer system 112 can exchange electronic messages with computer system 104 over a wired and/or wireless network. Thus, in response to a detected potentially actionable event and in addition to other automated actions, computer system 104 can also send an alarm message to computer system 112. For example, in response to detecting that patient 118 is attempting to exit support platform 103, computer system 103 can send alarm message 114 to computer system 112. Alarm message 114 can be sent in addition to computer system activating a height adjustment mechanism to lower support platform 103.

Alarm messages received at computer system 112 can alert health care provider of a potentially actionable event and/or notify health care provider of automated actions. For example, alarm message 114 can notify provider 113 that patient 118 is attempt to exit support platform 103 and/or that computer system 104 has initiated lower support platform 103. Provider 113 can confirm alarm messages received at computer system 112. Provider 113 can also send commands (e.g., response message 116) back to computer system 104. For example, upon switching to a video feed of patient location 101, provider 113 can observe that a portion of patient 118's body is under support platform 103. In response, provider 113 can send response message 116 to computer system 104 instructing computer system 104 to stop lowering support platform 103.

Provider 113 can also contact other providers, such as, for example, provider 119 in response to a detected potentially actionable event. Provider 113 can instruct other provides to physical enter patient location 101, access the health or patient 118, and take further appropriate actions to safeguard the health of patient 118.

In some embodiments, support platform 103 is rapidly (e.g., in two seconds or less) lowered to essentially floor level (e.g., zero to three inches above floor level) in response to determining correlation with a threshold probability that patient 118 is attempting to exit support platform 103. Accordingly, the potential fall distance for patient 118 can be reduced from some standard height, such as, for example, 21 inches (or any other current height) plus mattress width above floor level, to between zero to three inches plus mattress width above floor level before patient 118 can complete the attempted exit from platform support 103.

Alternately, or in combination with support platform lowering, the bed rails of a support platform can also be raised. Thus, alternately to or in combination with lowering support platform 103, one or more bedrails of support platform 103 can be raised from a lowered position to attempt to prevent the patient from exiting the support platform. Bedrails can be raised in response to determining that accessed (e.g., sensor and profile) data correlates with the threshold probability than the patient is attempting to exit support platform 103. For example, computer system 104 can raise bedrails of support platform 103 from a lowered position some higher position in response to determining that input from sensors 112 correlates with a threshold probability of patient 118 attempting to exit support platform 103. Raising the bed rails potentially prevents patient 118 from exiting support platform 103. Raising bed rails can occur within the same time constraints as lowering the support platform.

Utilizing Sensor Data to Monitor Patients

As previously described, a variety or different types and numbers of sensors can be utilized to monitor a patient and provide data used to detect a support platform exiting event. FIGS. 2 through 6C describe various examples of accessing sensor data from sensors that are monitoring a patient and detecting from the accessed input data that the patient is attempting to exit the patient support platform.

Figure 2:
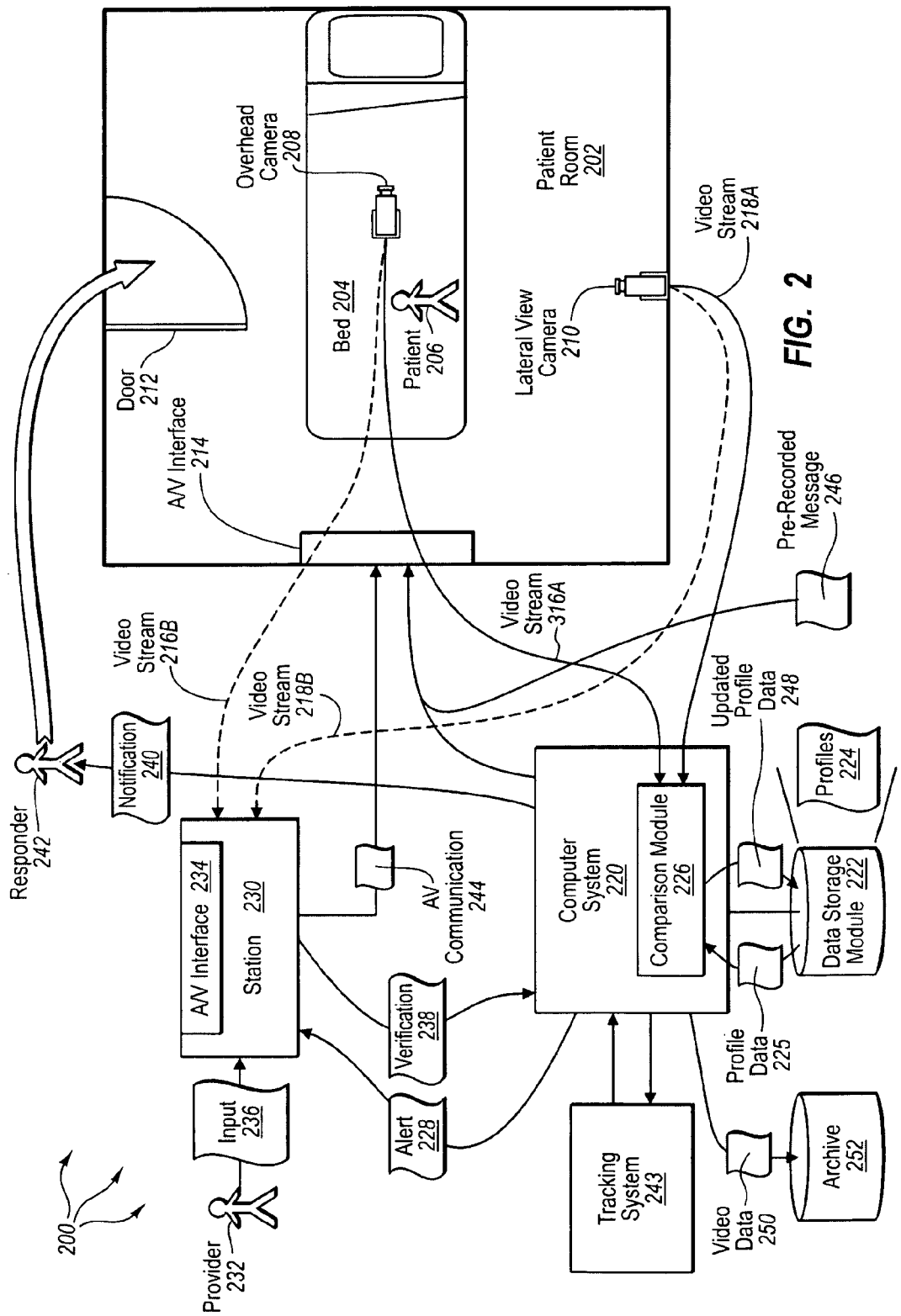
FIG. 2 illustrates an example system for patient monitoring, alert and response.

Referring now to FIG. 2, FIG. 2 is a diagram that schematically illustrates an exemplary computer controlled environment 200 for patient monitoring, more particularly with respect to monitoring potential support exiting, detecting a position and/or movement of a patient that is predictive of support exiting. Computer controlled environment 200 also facilities optionally obtaining human verification of actual support exiting and intervening if support exiting is confirmed.

Computer controlled environment 200 includes a patient room 202 containing a bed 204 or other support and a patient 206 resting thereon at least some of the time. One or more overhead cameras 208 may be provided that provide an aerial view of patient 206 together with one or more side cameras 210. The overhead camera 208 is especially useful in monitoring lateral (i.e., side-to-side) and longitudinal (i.e., head-to-foot) patient movements, although it may also monitor other movements. The side camera 210 is especially useful in monitoring longitudinal and up and down movements, although it can monitor other movements. The side camera or other camera (not shown) can be positioned to monitor and record a patient room door 212 or other access point (e.g., to record entry and/or exit of personnel, other patients, and visitors). The bed 204 may include markings (e.g., decals) (not shown) that assist in properly orienting the cameras.

The room 202 also includes an audio-video interface 214 that can be used to initiate one-way and/or two-communication with the patient 206. A/V interface 214 may include any combination of known A/V devices, e.g., microphone, speaker, camera and/or video monitor. According to one currently preferred embodiment, A/V interface 214 is mounted to a wall or ceiling so as to be seen by patient 206 (e.g., facing the patient's face, such as beyond the foot of the patient's bed). The A/V interface 214 includes a video monitor (e.g., flat panel screen), a camera mounted adjacent to the video monitor (e.g., below), one or more microphones, and one or more speakers. The A/V interface may form part of a local computer system (e.g., an "in room controller") that controls the various communication devices located in the patient room.

Cameras 208 and 210 (as well as any other cameras at a patient location) can continuously monitor patient 206 resting on bed 204 (or any other platform support). Cameras 208 and 210 (as well as any other cameras at a patient location) can capture a series of images of patient 206 resting on bed 204 (or any other platform support). The series of images can be captured as video data streams 216A and 218A and can be sent to computer system 220 for analysis.

Computer system 220 can receive video data streams 216A and 218A from cameras 208 and 210 respectively. Computer system 220 can analyze video data streams 216A and/or 218A to determine the position of patient 206 on bed 204. Computer system can compare the position of patient 206 to profile data 225 (profile data related to support exiting for patient 206).

According to one embodiment, at least a portion of the computer system 220 is an in room controller associated with (and potentially in) patient room 202. In the case where each patient room has its own in room controller, patient monitoring and analysis can be performed in parallel by dedicated in room controller computers. Nevertheless, at least some of the tasks, information, and information flow may be performed by a remote computer, such as a central facility master computer. Computer system 320 may therefore include multiple networked computers, such an in room controller, facility master, and other remote computers. The computer system 220 includes or has access to a data storage module 222 that includes patient profiles 224 (e.g., stored and updated centrally in the facility master and used locally by and/or uploaded to the in room controller).

A comparison module 226 of the computer system 220 can analyze the video streams 216A, 218A and, using one or more algorithms (e.g., that may be known in the art or that may be developed specifically for this system), determines the location and/or any movements of patient 206. This information is compared to patient specific profile data 225 from a patient profile 224 that corresponds to patient 206. In the absence of predicted support exiting or other triggering event, video streams 216A and 218A are typically not viewed by any human but are deleted or simply not stored or archived. This helps protect patient privacy.

When a location and/or movement of patient 206 matches or correlates with profile data 225 predictive of support exiting by patient 206, computer system 220 can activate a height adjustment mechanism of bed 204 to lower a corresponding support platform.

Optionally computer system 220 can also sends alert 228 to central station 230 (e.g., nurse's station) that patient 206 may be attempting to exit support 204. In addition to the alert 228, at least one of video streams 216B and 218B from cameras 208 and 210 and/or a modified video stream (not shown) from computer system 220 is sent to an A/V interface 234 at central station 230 for human verification of actual patient support exiting. The patient 206 is advantageously notified of potential active viewing by staff to satisfy HIPAA regulations (e.g., by a chime, prerecorded message, e.g., "camera is actively viewing", or visual indication, e.g., flashing or illuminated words, TV raster pattern). A provider 232 views the video stream(s) from patient room 202, determines whether the patient 206 is in fact preparing to exit the bed 204 or other support, and provides verification input 236 to an appropriate interface device (not shown) at station 230, which sends verification 238 to the computer system 220. Verification 238 may either confirm or reject the determination of patient support exiting. Verification 238 can also instruct computer system 220 to stop the lowering of a platform support if lowering would in fact be more harmful to patient 206. When viewing is terminated, the patient may be notified of this fact by, e.g., a tone or pre-recorded message ("active viewing is terminated").

If the provider 232 determines and verifies that actual patient support exiting is occurring or about to occur, the in room controller, facility master, or other appropriate module or subsystem component within computer system 220 can also send notification 240 to a responder 242 to assist patient 206. Notification 240 may be sent by any appropriate means, including an audio alert using a PA system, a text and/or audio message sent to a personal device carried by responder 242, a telephone alert, and the like. A tracking system 243 that interfaces or communicates with the computer system 220 (e.g., the facility master) may be used to identify a caregiver 242 who is assigned to patient 206 and/or who is nearest to patient room 202. In this way, direct physical assistance to patient 206 who may be attempting to exit support 204 can be provided quickly and efficiently in combination with lower a support platform.

In addition to or instead of sending notification 240 to responder 242, one- or two-way A/V communication 244 can be established between provider 232 at central station 230 and patient 206 (e.g., by means of A/V interfaces 214 and 234). This allows provider 232 to talk to patient 206 in order to provide instructions or warnings regarding support exiting, possibly to distract patient 206 and delay or prevent support exiting (e.g., "why are you getting out of bed?"). This may allow responder 242 to more easily intervene prior to actual support exiting so as to prevent or better mitigate potential harm to patient 206. A pre-recorded audio and/or A/V message 246 may alternatively be sent to A/V interface 214 in patient room 202 instead of direct A/V communication between provider 232 and patient 206.

In any event, whether or not a provider 232 is not present at central station 230 and/or fails to provide verification 238 regarding predicted support exiting within a prescribed time period, the computer system 220 may nonetheless initiate an automated response in order to prevent or mitigate potential harm to patient 206. An automated response can include any of: lowering a support platform of bed 204, sending notification 240 to a responder 242 regarding possible support exiting, and sending a pre-recorded message 246.

Verification 238, whether confirmation or denial of actual support exiting, can also be used to update the patient profile 224 corresponding to patient 206. Updated profile data 248 based on one or more support exiting events can be input or stored at data storage module 222. If a particular behavior is found to accurately predict support exiting by patient 206, the patient profile 224 can be updated to confirm the accuracy of the initial profile 224. In some cases, limits within the patient profile 224 may be tightened to be more sensitive to movements that have been confirmed to correlate with and accurately predict support exiting. This may be done manually by authorized personnel or automatically by the computer system 220. If, on the other hand, a particular behavior is determined to falsely predict support exiting by patient 306, the patient profile can be updated to note incidences of such false positives. Limits within the patient profile 224 can then be loosened or eliminated relative to any movements that have been found not to correlate with support exiting by patient 206. In the event support exiting by patient 206 occurs but is not detected by the computer 220, limits within the patient profile 224 can be established and/or tightened in an effort to eliminate false negatives of support exiting by patient 206. Updating the profile 224 of patient 206 to more accurately predict support exiting and reduce or eliminate false positive and false negatives substantially increases the reliability of the patient monitoring system as compared to conventional systems that do not distinguish between and among support exiting habits or behaviors of different patients.

In order to later view and/or analyze a triggering event as may be established by a facility, video data 250 that is the same as, or which may be derived from, one or both of video streams 216 and 218 can be stored within an archive 252. Archive 252 may comprise any storage media known in the art of video recording and storage, examples of which include hard drives, optical storage devices, magnetic tapes, memory devices, and the like.

Figure 3A:
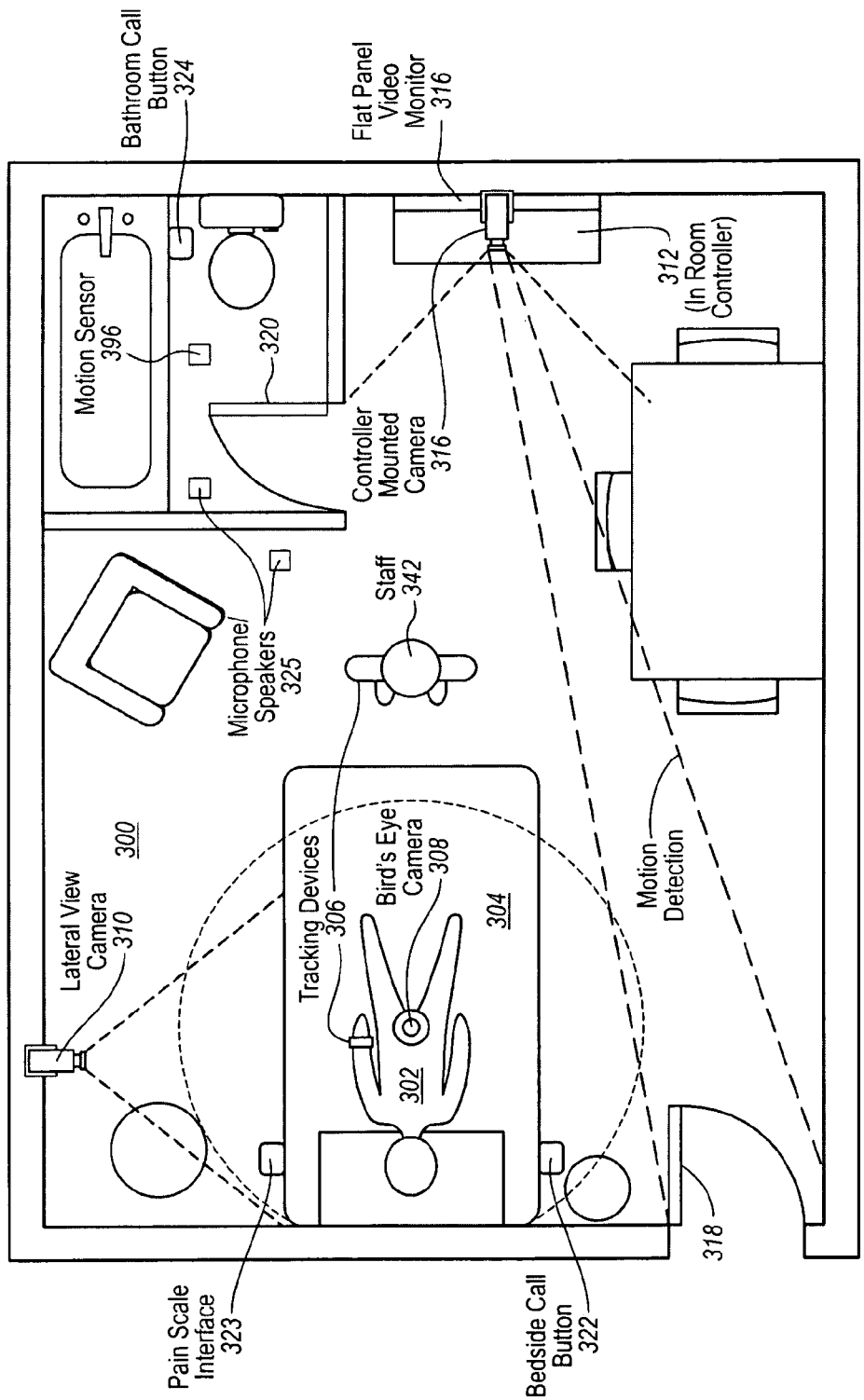
FIGS. 3A and 3B illustrate configurations of patient rooms at a healthcare facility equipped for patient monitoring and response to support exiting.
Figure 3B:
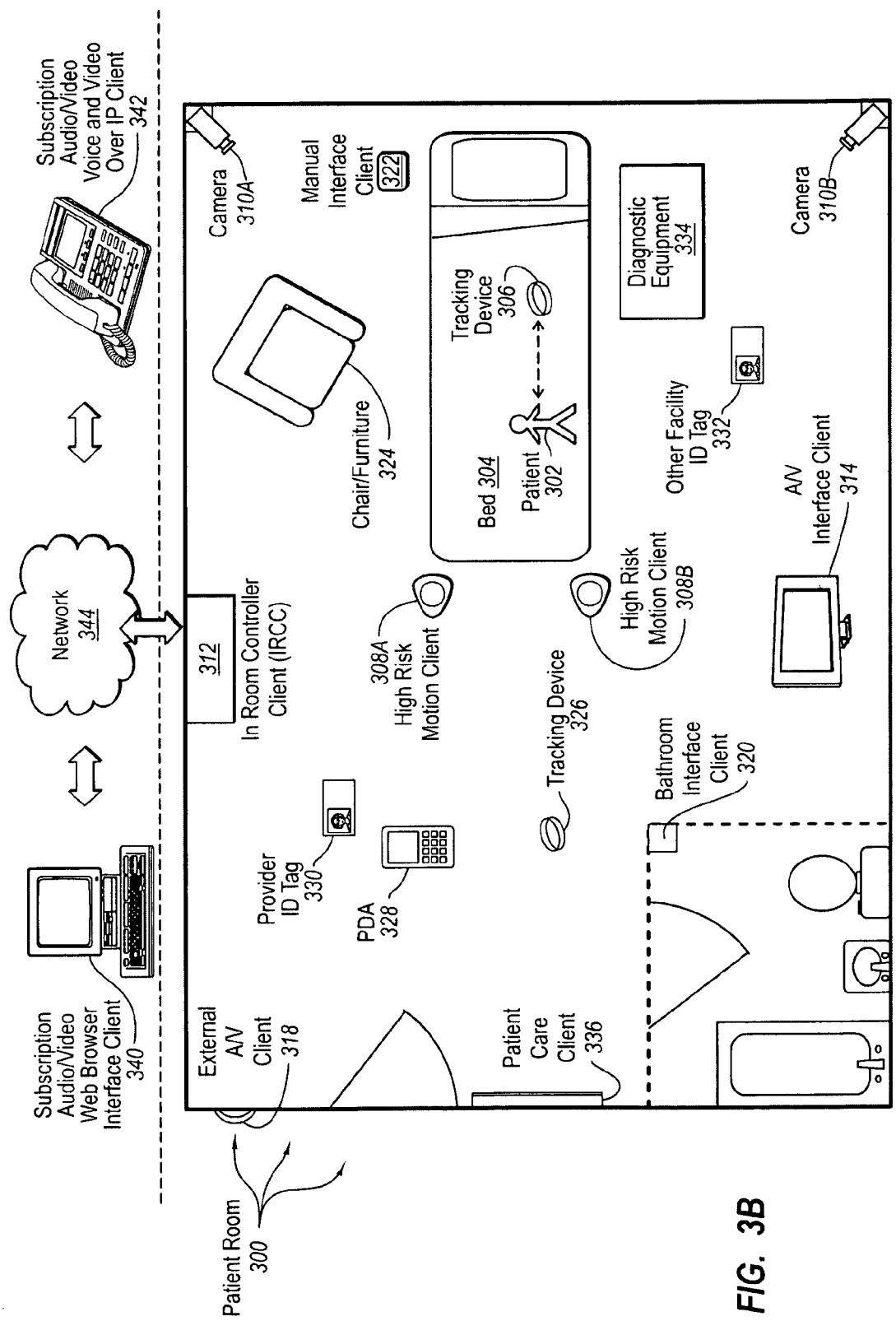

FIGS. 3A and 3B schematically illustrate exemplary configurations of patient rooms at a healthcare facility equipped for patient monitoring and response to support exiting.

In the embodiment of FIG. 3A, an exemplary patient room 300 is illustrated which includes a patient 302, a bed 304 or other support upon which the patient 302 rests at least some of the time. Patient 302 may wear or carry a mobile electronic tracking device 306, such as an RFID bracelet, ultrasound bracelet, or other device. This allows a facility master computer to identify and track the location of the patient 302 by means of electronic tracking systems known in the art. Device 306 is specially assigned to patient 302 and provides verification when patient 302 is located in room 300. This facilitates using the correct patient profile when interpreting movements of patient 302 rather than those of another patient.

One or more overhead cameras 308 are positioned above the bed 304 and so as to provide an aerial (e.g., bird's eye) view of patient 302. One more side cameras 310 are positioned to the side of patient 302 to provide a different data stream for determining the patient's position and/or movements. Camera 310 may have a direct or peripheral view of a door 318 or other entrance to room 300. An in room controller computer (IRCC) 312, which may be a local computer located in room 300, at least partially controls and is in communication with cameras 308, 310. A flat panel monitor 314 (e.g., high definition), controller mounted camera 316, and optionally other devices such as microphones and speakers (not shown) are interfaced with IRCC 312.

IRCC 312 is used to determine the location of the patients body, including specific body parts, by interpreting video data streams generated by one or more of the cameras and comparing relative distances between the patient's body and fixed locations (e.g., the patient's head and the headboard of the bed, the patient's arms and legs relative to the bedrails, the height of the patient's torso relative to the bed, etc.). A changing body part position indicates movement of that body part. IRCC 312 continuously or periodically compares the location and/or any movements of the patient's body or portion thereof with locations and movements predictive of patient bed exiting by that patient as contained in the patient's profile of bed exiting behaviors. Whenever a position and/or movement is detected that is consistent with bed exiting, an appropriate response is initiated as discussed elsewhere.

The flat panel video monitor 314 can provide multiple functions, including providing normal television programming, recorded programming requested by the patient 302, video feeds remote locations (such as loved ones and staff who wish to communicate with patient 302 remotely), and special messages (e.g., patient alerts). The controller mounted camera 316 provides a direct facial view of the patient and, in combination with video monitor 314, facilitates two-way A/V communication between patient 302 and person's outside room 300. As shown, the camera 316 may also have a direct view of a door 318 or other entrance to monitor entry and exit of persons (e.g., staff 3 32) from room 300. Camera 316 may also have a view of bathroom door 320 to monitor movement of patient 302 to and from the bathroom. A standard motion sensor integrated with conventional video cameras (e.g., camera 316) may provide motion detection means for monitoring room entry or exiting activity.

The room 300 may include other auxiliary devices, such as bedside call button 322, bedside patient pain scale interface 323, bathroom call button 324, microphones/speakers 325, and bathroom motion sensor 396. Call buttons are known in the art. The pain scale interface 323 allows a patient to indicate to the monitoring system (e.g., IRCC 312, facility master, and/or nurse's station) the patient's current pain level (e.g., on a scale of 1 to 10, with 1 being the least and 10 being the most pain). Motion sensor 396 can be used, e.g., in combination with camera 316, call button 324 and/or microphones/speakers, to determine whether a patient 302 requires further assistance while in the bathroom. An RFID grid set up throughout the room can be used to monitor the position and/or movements of the patient 302 when not resting on the bed 304, as well as the position and/or movements of staff 3 32, other persons such as patients, friends, family or other visitors, and assets (not shown).

FIG. 3B illustrates an exemplary patient room 350 which includes a patient 302, a bed 304 or other support upon which the patient 302 rests at least some of the time, and various other devices used to monitor the patient and the patient's room 350. The patient 302 may wear or carry a mobile electronic tracking device 306. This allows a facility master computer to identify and track the location of the patient 302 by means of electronic tracking systems known in the art. Tracking device 306 may be a conventional RFID device or ultrasound device (e.g., bracelet) and may be equipped with a patient call or panic button (not shown) as known in the art. Tracking device 306 is specially assigned (and attached) to patient 302 staying in patient room 350. Tracking device 306 provides verification that patient 302 is actually located in room 350. This facilitates using the correct patient profile when interpreting movements of patient 302 rather than those of another patient.

High risk motion clients 308A and 308B (e.g., which include one or more of cameras, electronic motion sensors, electric eyes, RFID detectors, ultrasound detectors, etc.) may be positioned on either side of bed 204, thus providing two separate data streams for interpretation of the patient's position and/or movements. Side cameras 310A and 310B are positioned on either side of patient 302 to provide additional data streams for interpretation of the patient's position and/or movements. At least one of cameras 310A and 310B may have a direct or peripheral view of a door 311 or other entrance to room 300. An in room controller client (IRCC) 312, which can be a local computer located in or near room 350, at least partially controls motion clients 308A and 308B, cameras 310A and 310B, and other electronic devices in room 350. IRCC 312 also analyzes video data generated by cameras 308, 310 in order to identify behavior of patient 302 that may be predictive of support exiting.

Other electronic devices include an in-room A/V interface client 314, which can be used to establish one- or two-way communication with patient 302, patient care client 336, external A/V client 318 (e.g., in a hallway), bathroom interface 320 (e.g., call button, microphone and/or speaker), and manual patient interface client 322 (e.g., a call button, pain scale dial, etc.). The room is shown having a chair 324 or other furniture (e.g., wheel chair), upon which visitors or even the patient may rest at least some of the time. The monitoring system can be used to detect potential support exiting by patient 302 of chair/furniture 324 in addition to bed 204.

IRCC 312 and electronic devices in room 350 can interoperate to implement the principles of the present invention. High risk motion clients 308A and 308B, either alone or in combination with one or both of cameras 310A and 310B, can monitor a patient's movements in bed 204 and/or chair or other furniture 324. Generally, a patient's movement on a bed or other support can be monitored through a grid monitoring system ("GMS") that identifies patient vertical and horizontal movements that may be indicative of an attempt to exit the furniture. The time a body part is located within a critical zone and/or changes in position and/or changes in speed can all be determined. The GMS can also utilize pressure, temperature, and other distributed sensors located within a bed or other furniture or directly attached to a patient. Inputs from the various clients and sensors in room 350 can be provided to IRCC 312 and/or facility master (not shown). In addition, any of cameras 310A, 310B or 320, as well as motion clients 308A and 308B, can monitor a patient's position and/or movements within room 350 when the patient is not resting on a bed 304, chair 324 or other support located in room 350.

Upon activation of the GMS or other high risk motions clients, in room controller client 312 and/or a facility master utilizes patient management software to initiate and establish automated responsive actions. For example, upon detecting activities that predict an unattended support exit, in room controller 312 and/or a facility master can automatically activate a height adjust mechanism of bed 304 to lower a corresponding support platform. In addition, in room controller 312 and/or a facility master can optionally establish a real time A/V connection with a central station (e.g., nurse's) and/or one or more mobile caregiver clients (e.g., PDAs carried by responder caregivers). Further, in room controller client 312 and/or a facility master can activate external A/V client 318 (e.g., an alarm in a hallway) and/or initiate archiving of data from one or more of high risk motion clients 308A and 308B, and cameras 310A, 310B and 320 upon the occurrence of a support exiting event or other pre-established triggering event.

FIG. 3B further depicts a provider tracking device 326 (e.g., an RFID or ultrasound device), a provider PDA 328, a provider ID tag 330 (e.g., an RFID or ultrasound device), other facility ID tag 332 (e.g., an RFID or ultrasound device), and/or diagnostic equipment 334 which have entered room 350. Each of these devices can communicate with IRCC 312 and/or a system-wide tracking system that communicates direct to a facility master computer (not shown) via various appropriate protocols (e.g., RF, ultrasound waves, IEEE 802.11 group, IEEE 802.15.4, etc.). IRCC 312 can update pertinent patient information, such as, for example, provider ID, other personnel ID or diagnostic equipment and time of entry. Detecting the presence of personnel and devices inside room 350 indicates that facility personnel and/or assets associated with these devices have likely entered room 350, for example, in response to a predicted support exiting event, a patient initiated alarm, prescribed patient activities, and the like.

According to one embodiment, patient room 350 may be networked with other components including, for example, subscription clients (e.g., subscription A/V web browser interface client 330 and subscription A/V voice and video over IP client 342), which are connected to in room controller client 312 by means of network 344. Subscriber clients 340 and 342 can be located at or external to a healthcare facility. Thus, providers in diverse locations can be notified of actionable events occurring inside patient room 350.

Figure 4A:
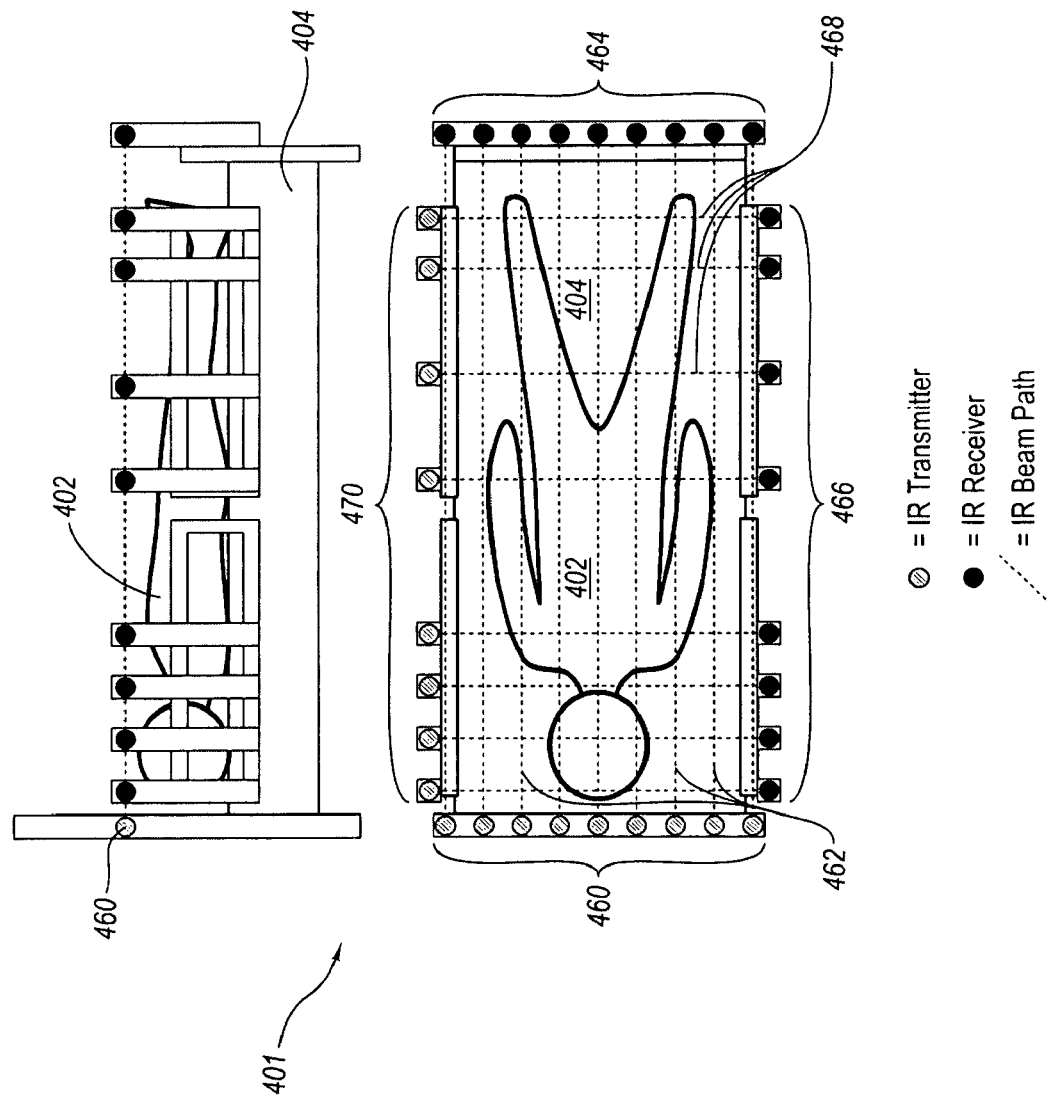
FIG. 4A depicts components for detecting patient support exiting behavior comprising a light beam matrix system.

FIG. 4A depict embodiments for detecting patient support exiting behavior comprising a light beam matrix system 401. A light beam matrix system can be used instead of or in addition to other detection mechanisms (e.g., cameras) to demine patient positions and/or movement. Light beam matrix system 401 includes a patient 402 resting on a bed 404 or other support. A plurality of light transmitters 460 are positioned at one side of bed or other support 404 and generate first beams of light 462, which are detected by corresponding first light receivers 464. A plurality of second light transmitters 466 are positioned laterally relative to first light transmitters 460 and generate second beams of light 468, which are detected by corresponding second light receivers 470. Beams of light 462, 468 may comprise IR, visible or UV wavelengths. Transmitters 460 and 470 and receivers 464 and 466 can be sensors included in sensors 112.

First and second beams of light 462, 468 may be positioned above the patient 402 and cross-cross to form a light beam matrix that is able to detect patient location and/or movement in multiple (e.g., three) dimensions. The closer together the light beams, the finer the detection of patient position and/or movement. According to one embodiment, the light beams are spaced apart at intervals ranging from 6 inches to 2 feet (e.g., at 1 foot intervals). As long as the patient 402 rests flat on the bed or other support 404 or is otherwise below the light beam matrix comprising first and second light beams 462, 468, no beams of light are blocked or interrupted such that no movement is detected. Interrupting and/or resuming one or more beams of light may be indicative up upward and/or downward movement(s). Sequentially interrupting and/or resuming one or more of first light beams 462 may be indicative of lateral movement(s). Sequentially interrupting and/or resuming one or more of second light beams 462 may be indicative of longitudinal movement(s).

A computer system, such as, for example, any of computer system 104, a facility master, and an in room controller client, interprets data (e.g., sensor data 122) generated by the light beam matrix. Continuous light detection by the light sensors may be interpreted as a series of 1s (or 0s) in computer language. Any interruption or blocking of a light beam corresponds to a series of 0s (or 1s) in computer language and is indicative of a body part being positioned between one or more light particular light transmitters and detectors. Because bed exiting, for example, involves at least some lifting of the patient's body (e.g., to get over bed rails or pass through a narrow passage in a bed rail), actual lifting of the patient's body will typically block or interrupt at least one light beam. Depending on which light beams are interrupted, the computer can determine which parts of the patient's body have raised and/or moved. Crossing multiple beams typically indicates movement (i.e., lateral, longitudinal, upward and/or downward depending on which sequence of beams are interrupted). The patient's movements, as detected by the light beam matrix and interpreted by the computer system, are compared to a patient profile of positions and/or movements that are predictive of support exiting by that patient. If potential patient support exiting is detected, an appropriate response, such as, for example, automated lowering of a support platform, can be initiated.

Figure 4B:
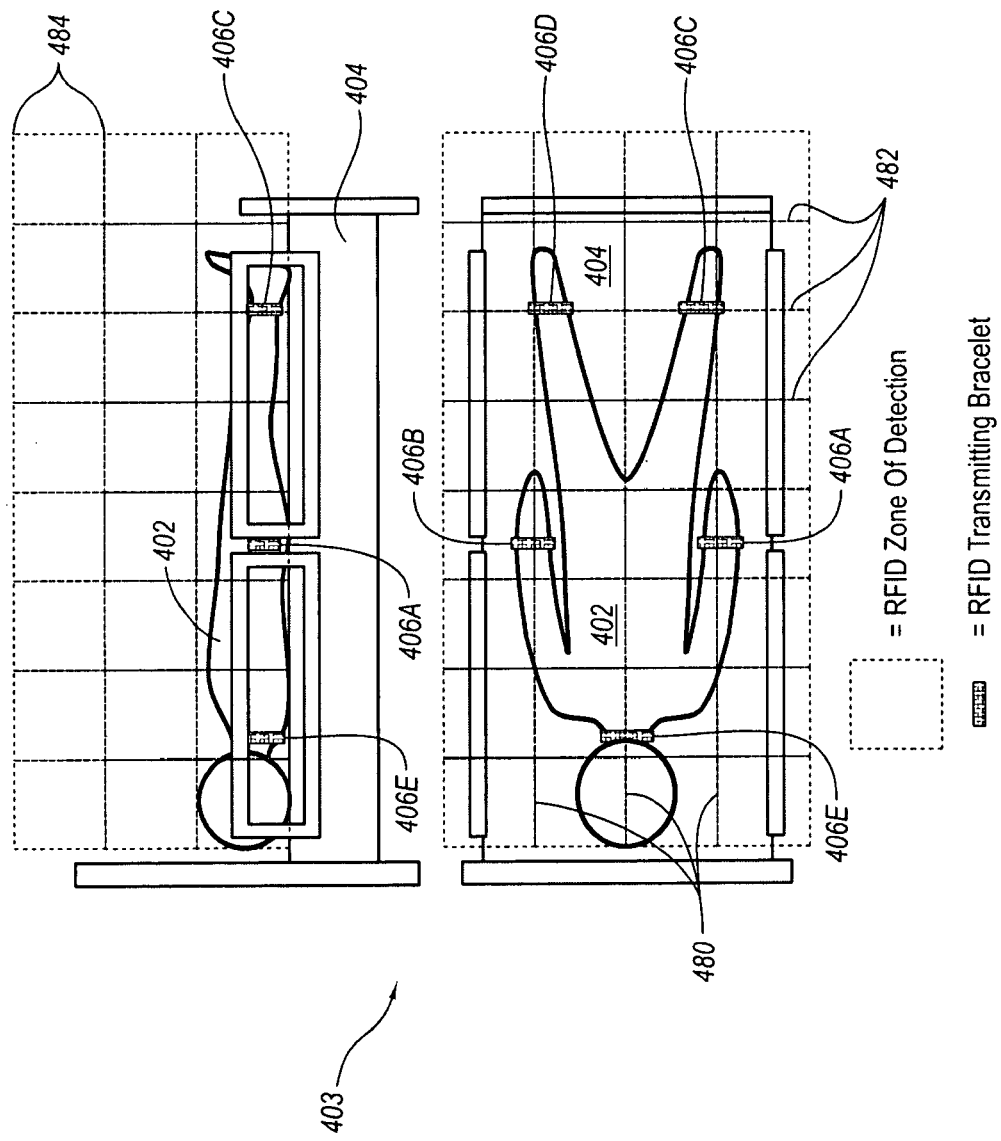
FIG. 4B depicts components for detecting patient support exiting behavior comprising a small zone RFID grid system.

FIG. 4B illustrates an alternative embodiment for detecting patient support exiting behavior comprising a small zone RFID grid system 403, which may be used instead of or in addition to other detection mechanisms (e.g., cameras) to demine patient positions and/or movement. RFID grid system 403 includes a patient 402 resting on a bed 404 or other support. The patient's body may be equipped with any appropriate number of RFID devices that are located so as to detect patient positions and/or movements associated with support exiting (e.g., right RFID wrist device 406A, left RFID wrist device 406B, right RFID ankle device 406C, left RFID ankle device 406D, and neck RFID device 406E). Each RFID device can be separately encoded to represent a specific body part of the patient to distinguish between positions and movements of the different body parts.

The RFID grid system 403 includes a three-dimensional grid of small, cube-like RFID zones defined by a plurality of RFID detectors positioned along lateral zone boundaries 480, longitudinal zone boundaries 482, and elevation zone boundaries 484. The closer together the RFID detectors, the finer the detection of patient position and/or movement. According to one embodiment, the RFID detectors are spaced apart at intervals ranging from 6 inches to 2 feet (e.g., at 1 foot intervals). The grid of RFID zones is able to detect three-dimensional patient position and/or movements as approximated by the positions and/or movements of the RFID devices 406 worn by the patient in or through the RFID zones. RFID devices 406A through 406E and RFID detectors can be included in sensors 112.

A computer system such as, for example, any of computer system 104, facility master, and in room controller client 412, interprets data (e.g., sensor data 122) generated by the small zone RFID grid as it detects the position and/or movement of the RFID devices 406 attached to the patient 402. Depending on which RFID zone is occupied by a specific RFID device and/or which RFID device(s) may be moving between RFID zones, the computer can determine the position and/or location of corresponding body parts of the patient. If potential patient support exiting is detected, an appropriate response such as, for example, automated lowering of a support platform, can be initiated.

A similarly configured ultrasound grid system can also be used to implement the functionality depicted in FIG. 4B. A patient's body may be equipped with any appropriate number of ultrasound devices that are located so as to detect patient positions and/or movements associated with support exiting. Each ultrasound device can be separately encoded to represent a specific body part of the patient to distinguish between positions and movements of the different body parts.

Thus, an ultrasound grid system can also include a three-dimensional grid of small, cube-like ultrasound zones defined by a plurality of Ultrasound detectors positioned along lateral zone boundaries 480, longitudinal zone boundaries 482, and elevation zone boundaries 484. The closer together the ultrasound detectors, the finer the detection of patient position and/or movement. According to one embodiment, the ultrasound detectors are spaced apart at intervals ranging from six (6) inches to two (2) feet (e.g., at one (1) foot intervals). The grid of ultrasound zones is able to detect three-dimensional patient position and/or movements as approximated by the positions and/or movements of the ultrasound devices worn by the patient in or through the ultrasound zones. Ultrasound devices and ultrasound detectors can be included in sensors 112.

Accordingly, a computer system, such as, for example, any of computer system 104, a facility master, and in room controller client 412 can interpret data (e.g, sensor data 122) generated by the small zone ultrasound grid as it detects the position and/or movement of the ultrasound devices attached to the patient 402. Depending on which ultrasound zone is occupied by a specific ultrasound device and/or which ultrasound device(s) may be moving between ultrasound zones, the computer can determine the position and/or location of corresponding body parts of the patient. If potential patient support exiting is detected, an appropriate response such as, for example, automated lowering of a support platform, can be initiated.

Types of Support Exiting Behaviors

FIGS. 5A-5E schematically depict a patient in various exemplary positions on a bed relative to known bed exiting behaviors.

Figures 5A, 5B, 5C, 5D, 5E:
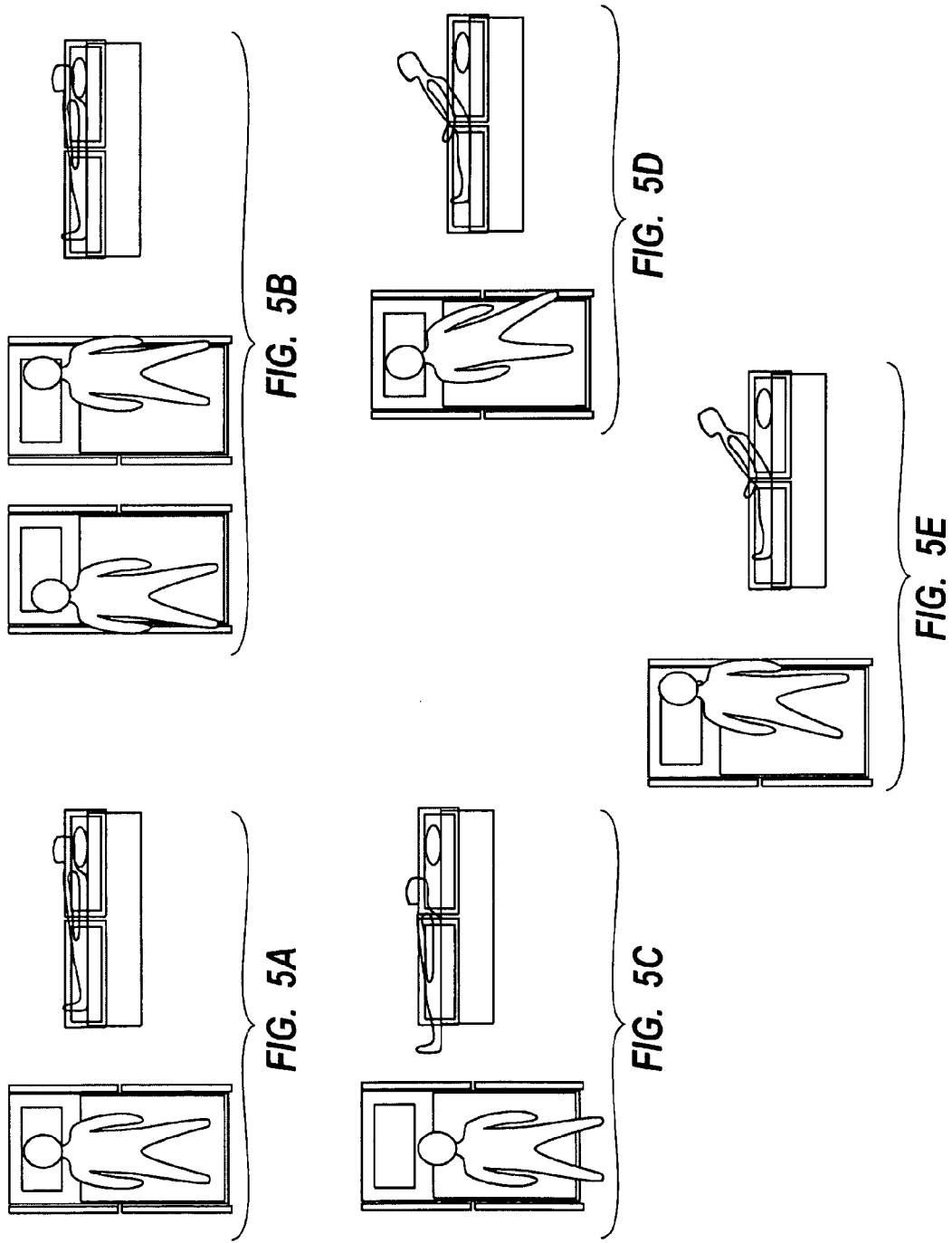
FIGS. 5A-5E depict a patient in various exemplary positions on a bed relative to known bed exiting behaviors.

FIG. 5A schematically illustrates a normal resting position of a patient lying flat on a bed. FIGS. 5B-5E schematically illustrate positions associated with various bed exiting positions, movements or behaviors that can be detected. FIG. 5B roughly depicts the position of a patient that has engaged in the bed slide method of bed exiting. A notable feature is the distance between the patient's head and the pillow or headboard. FIG. 5C illustrates left and right side rail roll methods in which the patient's body moves to the side or left side rail preparatory to bed exiting. FIG. 5D illustrates the torso up and leg swing left method of bed exiting, which is characterized by upward movement of the torso coupled with movement of the left leg toward the edge of the bed. The torso up and right leg swing method is simply the mirror image of that shown in FIG. 5D. FIG. 5E illustrates the torso up and upper body roll left method, which is characterized by the patient's torso moving upward and the patient's body rolling to the left. The torso up and upper body roll right method would be the mirror image of that shown in FIG. 5E.

Accordingly, configurable patient related data, such as, patient profiles, can contain one or more spatial parameters associated with the one or more support exiting behaviors that are known for each patient. The spatial parameters relating to bed exiting may include data points pertaining to one or more of the common bed exiting behaviors noted above. Image parameters relating to exiting of other supports can be tailored to behaviors that are typical for patients exiting such supports. Patient profiles may include idiosyncratic information that is specific to a particular individual (e.g., base on patient height, weight, speed of movement, length of limbs, number of operable limbs, and/or personal habits of position and/or movement while support exiting).

By way of example, as illustrated a spatial parameter that corresponds to the bed slide method of bed exiting is the distance from a head feature to the top of the bed (e.g., headboard) (see FIG. 5B). Spatial parameters corresponding to the side rail roll methods (left or right) for bed exiting include: (a) the torso positioned primarily to the right or left of the bed and (b) the hand and/or arm on or over (i.e., covering or blocking the view of) the left or right bed rail for a given period of time (see FIG. 5C). Spatial parameters corresponding to the torso up and leg swing methods (left or right) of bed exiting include: (a) the head elevated from a flat position and (b) right or left legs and/or feet breaking a vertical bed edge plane (see FIG. 5D). Spatial parameters corresponding to the torso up and upper body roll methods (left or right) of bed exiting include: (a) the head elevated from a flat position; (b) torso positioned primarily to the right or left portion of the bed; and one or both of ($c_1$) the left or right hand and/or arm on or over (i.e., covering or blocking the view of) the left or right bed rail for a given period of time and/or ($c_2$) the head breaking a vertical plane of the left or right side rail (see FIG. 5E). In addition to patient body position, time of duration of a limb or body part at a specified location relative to a critical region of the support may also play a roll in determining bed or other support exiting.

Accordingly, embodiments of the invention include accessing a predetermined set of spatial coordinates in a multi-dimensional coordinate space including and surrounding a support platform. The predetermined spatial coordinates identifying locations on or surrounding the support platform that, if a portion of a patient's body is detected therein, are indicative of the patient preparing to exit the support platform. The patient is continuously monitored by capturing a series of images of the patient and support to determine the patient's position relative to the support within the coordinate space. The patient's position within the coordinate system is periodically compared with the predetermined spatial coordinates. It is then determined whether the patient's position correlates to spatial coordinates indicative of attempted platform support exiting. In response to the position of the patient correlating with the predetermined spatial coordinates, automated lowering of the support platform can be initiated to prevent or mitigate harm to the patient.

In other embodiments, patient movements, as detected by one or more monitoring cameras (overhead, side view, and other) are converted into a 3-D patient data set. Patient data sets are compared to a library of data sets generated from known behavioral activities (e.g., reaching for a TV remote, rolling over side bedrail, etc.). A best correlation between data sets determines alert/no alert response. Configurable patient related data (e.g., a patient profile) influences best correlation choices via weighting factors.

Responding to a Support Exiting Event

Figure 11:
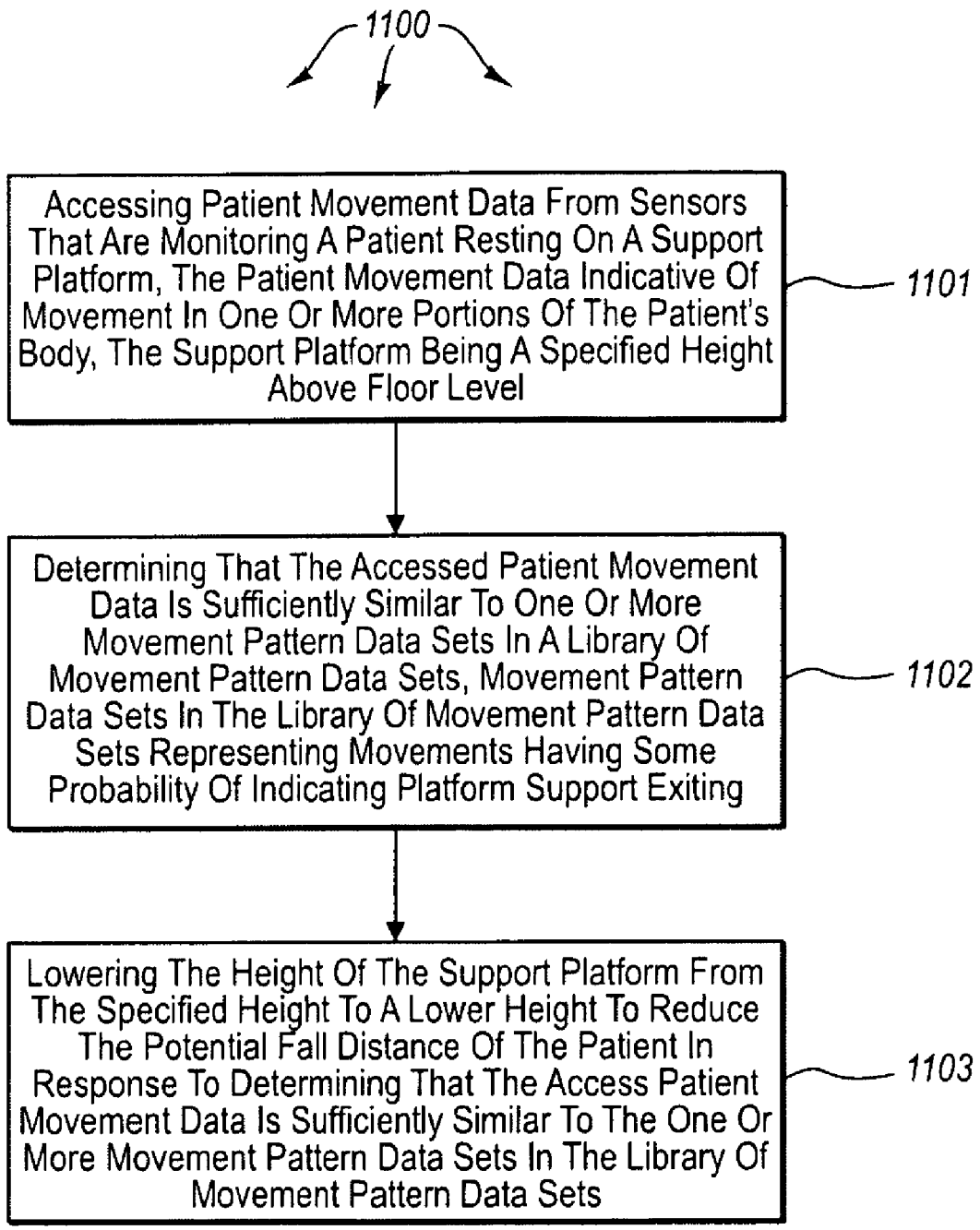
FIG. 11 illustrates a flow chart of an example method for responding to a support exiting event.

Referring now to FIG. 11, FIG. 11 illustrates a flow chart of an example method 1100 for responding to a support exiting event. The method 1100 will be described with respect to the components in patient room 300.

Method 1100 includes an act of accessing patient movement data from sensors that are monitoring a patient resting on a support platform, the patient movement data indicative of movement in one or more portions of the patient's body, the support platform being a specified height above floor level (act 1101). For example, IRCC 312 can access patient movement data from one or more of cameras 308(a,b), 310(a,b), and 316 that are monitoring patient 302 resting on bed 304. The patient movement data can indicate movement of one or more portions of patient 302's body. Initially, bed 304 can be a specified height (e.g., approximately 21 inches) above floor level of patient room 300.

Method 1100 includes determining that the accessed patient movement data is sufficiently similar to one or more movement pattern data sets in a library of movement pattern data sets, movement pattern data sets in the library of movement pattern data sets representing movements having some probability of indicating platform support exiting (act 1002). For example, IRCC 312 can store one or more movement patterns representing movements having some (e.g., increased) probability of indicating exiting from bed 304. Movement patterns can be stored in a general movement library applicable to all patients and/or in a patient profile specific to patient 302.

Some patient movements indicative of support platform exiting may be common to many or at least a large subset of patients that attempt to exit a support platform. For example, sweeping legs to one side of a bed may be a common way that most patients move their legs off a bed before attempting to place their feet on the ground. Common patient movements indicative of higher probabilities of support platform exiting can be stored in a general movement library.

Other patient movements indicative of support platform exiting may be specific to a particular patient when the particular patient attempts to exit a support platform. For example, due to medical or other physical conditions a particular patient may be incapable of performing more common movements indicative of support exiting. Alternately, a patient's movement may differ from more common movements simply as a matter of preference. Patient specific movements indicative of platform support exiting can be stored (and refined) in a patient profile.

Accordingly, IRCC 312 can compare accessed movement data for patient 302 to a movement data in a general movement library as well as in a patient profile for patient 302. Through comparison, IRCC 312 can attempt to identity similarities between the accessed movement data and any stored movement patterns having an increased probability of support platform exiting for patient 302. If sufficient similarity is identified between accessed movement data and a stored movement pattern (either general or specialized), IRCC 312 determines (or at least infers) that patient 302 is attempting to exit bed 304.

Method 1100 includes an act of lowering the height of the support platform from the specified height to a lower height to reduce the potential fall distance of the patient in response to determining that the access patient movement data is sufficiently similar to the one or more movement pattern data sets in the library of movement pattern data sets (act 1103). For example, IRCC 312 can lower bed 304 from its specified height to some lower height in response to determining that movement data from one or more of cameras 308(a,b), 310 (a,b), and 316 is sufficiently similarly to one or more movement pattern data sets generally and/or specifically indicative of an attempt by patient 302 to exit bed 304. Lowering of support platform reduces the potential fall distance of patient 302.

In some embodiments, bed 304 is rapidly (e.g., in two seconds or less) lowered to essentially floor level (e.g., zero to three inches above floor level) in response to identifying similarity between accessed movement data and movement pattern data indicative of patient 302 attempting to exit bed 304. Accordingly, the potential fall distance for patient 302 can be reduced from some standard height, such as, for example, 21 inches (or any other current height) plus mattress width above floor level, to between zero to three inches plus mattress width above floor level before patient 302 can complete the attempted exit from bed 304.

Alternately, or in combination with support platform lowering, the bed rails of a bed 304 can also be raised. Thus, alternately to or in combination with act 1103, method 1100 can include an act of raising one or more bedrails of bed 304 from a lowered position to attempt to prevent the patient from exiting bed 304 in response to identifying similarity between accessed movement data and movement pattern data indicative of patient 302 attempting to exit bed 304. For example, IRCC 312 can raise bedrails of bed 304 from a lowered position some higher position in response to determining that accessed movement data from one or more of cameras 308 (a,b), 310(a,b), and 316 is sufficiently similarly to one or more movement pattern data sets generally and/or specifically indicative of an attempt by patient 302 to exit bed 304. Raising the bed rails potentially prevents patient 302 from exiting bed 304. Raising bed rails can occur within the same time constraints as lowering the support platform.

Similar accessing of movement data, comparing of accessed movement data to movement data sets, and responding to support exiting events can be implemented for light beam matrix system 401 and RFID grid system 403.

Digital Interpretation of Data Indicative of Support Platform Exiting

In some embodiments, platform support exiting is detected through digital interpretation of video data. Detecting support platform exiting behaviors through digital interpretation of video data can include:

Camera Calibration. One or more video cameras (e.g., 308, 310, and 316) view a patient bed. Visually distinguishable features on the bed are utilized (and potentially digitized) to outline the area of the bed and to orient the angular/positional relationship between the cameras and bed.

Bed Defining. Utilizing the calibrated camera orientation, a computer system (e.g., computer system 104, computer system 220, in room client controller 312, a facility master computer systems, etc.) models the patient bed based on (potentially digitized) data provided by the cameras. The bed model is used as a reference against which patient movement patterns will be registered and measured.

Scene Modeling. The computer system also defines static background elements (areas outside the bed) and dynamic foreground elements (within bed areas) within the cameras' view based on data provided by the cameras.

Foreground Movement Tracking. Movement data representing changes in the composition of the foreground image (i.e., within the bed area) are digitized and grouped into individual clusters of activity. These clusters are tracked both positionally and temporally. The combination of cluster movement (relative to the bed coordinates) and cluster velocity form unique data sets capturing patient movement behaviors.

Behavior Data Set Library. As a unique patient movement data set is being generated for a particular patient, the data set is continuously compared to a library of behavioral data sets. Best fit calculations are performed to mathematically assess the degree of correlation between the evolving patient data set and pre-existing behavior patterns. The behavior data set library may contain generic movement pattern data useful for predicting support exiting for some or all patients as well as unique movement pattern data collected from the individual patient (e.g., stored in a patient profile) being currently monitored useful for predicting support exiting of the specific patient. Refinement to the best fit calculations may occur through addition of behavioral weighting factors, residing within individual patient profiles. Increased behavioral weighting factors would be assigned to bed exiting patterns that show a historical preference by the individual patient under observation. Therefore, the best fit interpretation of the currently observed movement pattern can be influenced, at least in part, by the historically exhibited bed exiting behaviors of the monitored patient.

Automated Response. When adequate correlation is measured between the currently exhibited patient movement pattern and a library movement pattern that is deemed to be dangerous (e.g., predictive of support exiting), an automated response, such as, for example, automated lowering of a support platform, transmitted an alert to caregivers, etc, is initiated.

Figure 6A:
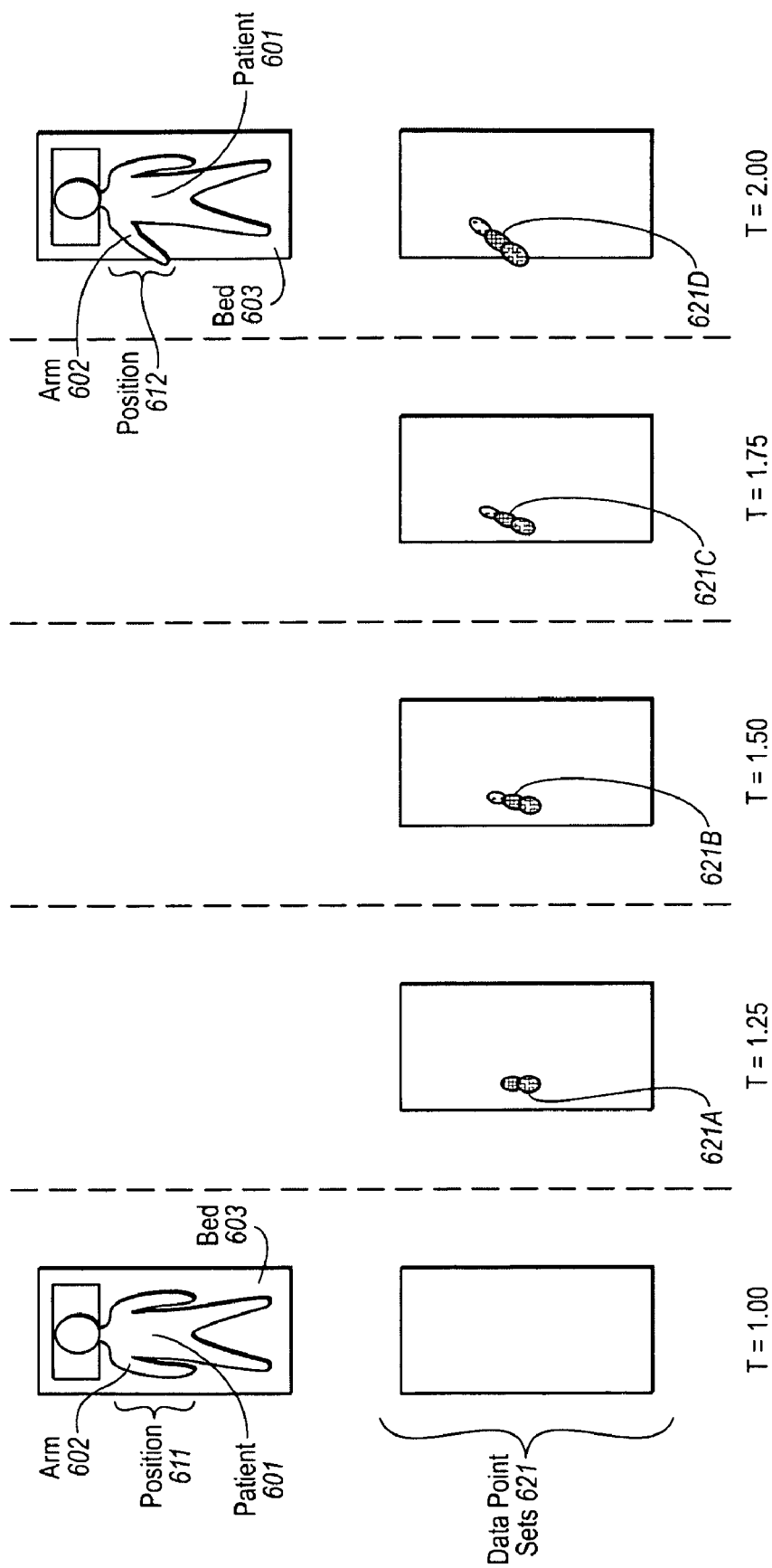
FIG. 6A schematically illustrates a patient lying on a bed at two different time intervals and data point sets that are generated through motion capture analysis between the time intervals.

FIG. 6A depicts patient 601 lying on bed 603 at two different time intervals and data point sets that are generated through motion capture analysis between the time intervals. Bed 603 can previously have been modeled based on data received from cameras in patient 601's room, such as, for example, cameras 308, 310, and 316. The model of bed 603 can be used as a reference to register and measure movement patterns of patient 601.

Thus, it may be that patient 601 is monitored by one or more video cameras, including cameras 308, 310, and 316. Accordingly, the video cameras can monitor that at time T=0.00 arm 602 is in position 611. Over the course of some amount of time (e.g., some number of seconds), the video cameras can monitor that arm 611 is moved to position 602 at time T=1.0.

At specified time intervals, for example, every 0.25 time units (seconds), a computer system (e.g., computer system 104, computer system 220, in room client controller 312, a facility master computer systems, etc.) can analyze video streams from the cameras and capture a set of data points representing a motion mapping of a patient's movement. For example, data point sets 621 can generated in response to detecting movement of arm 602 from position 611 (beside patient 601's body) to position 612 (e.g., reaching for the right bedrail). Data point set 621A can be generated at time T=1.25, data point set 621B can be generated at time T=1.50, data point set 621C can be generated at time T=1.75, and data point set 621D can be generated at time T=2.00.

Captured data points across time intervals can be used to generate movement patterns for patient 601. For example, data point sets 621 can be used to generate movement patterns for different parts of arm 602. Individual movement patterns can be combining with one another into a motion capture pattern summary.

FIG. 6B illustrates a motion capture pattern summary 631 for patient 601. Motion capture pattern summary 631 includes captured movement of different portions of arm 611. For example, movement pattern 631A can represent the movement of arm 611 near the right shoulder of patient 601. Movement pattern 632A can represent the movement of arm 611 near the elbow of arm 611. Movement pattern 632C can represent the movement of arm 611 near the wrist of arm 611. Movement pattern 632D can represent the movement of arm 611 near the hand of arm 611.

Movement patterns having thicker lines indicate increased speed of movement. On the other hand, movement patterns having thinner lines indicate decreased speed of movement. Thus, from motion capture pattern summary 631, it can be determined that the hand of arm 611 (movement pattern 631D) moved faster than the elbow of arm 611 (movement pattern 631B) during the time interval between T=1.00 and T=2.00.

Figure 6C:
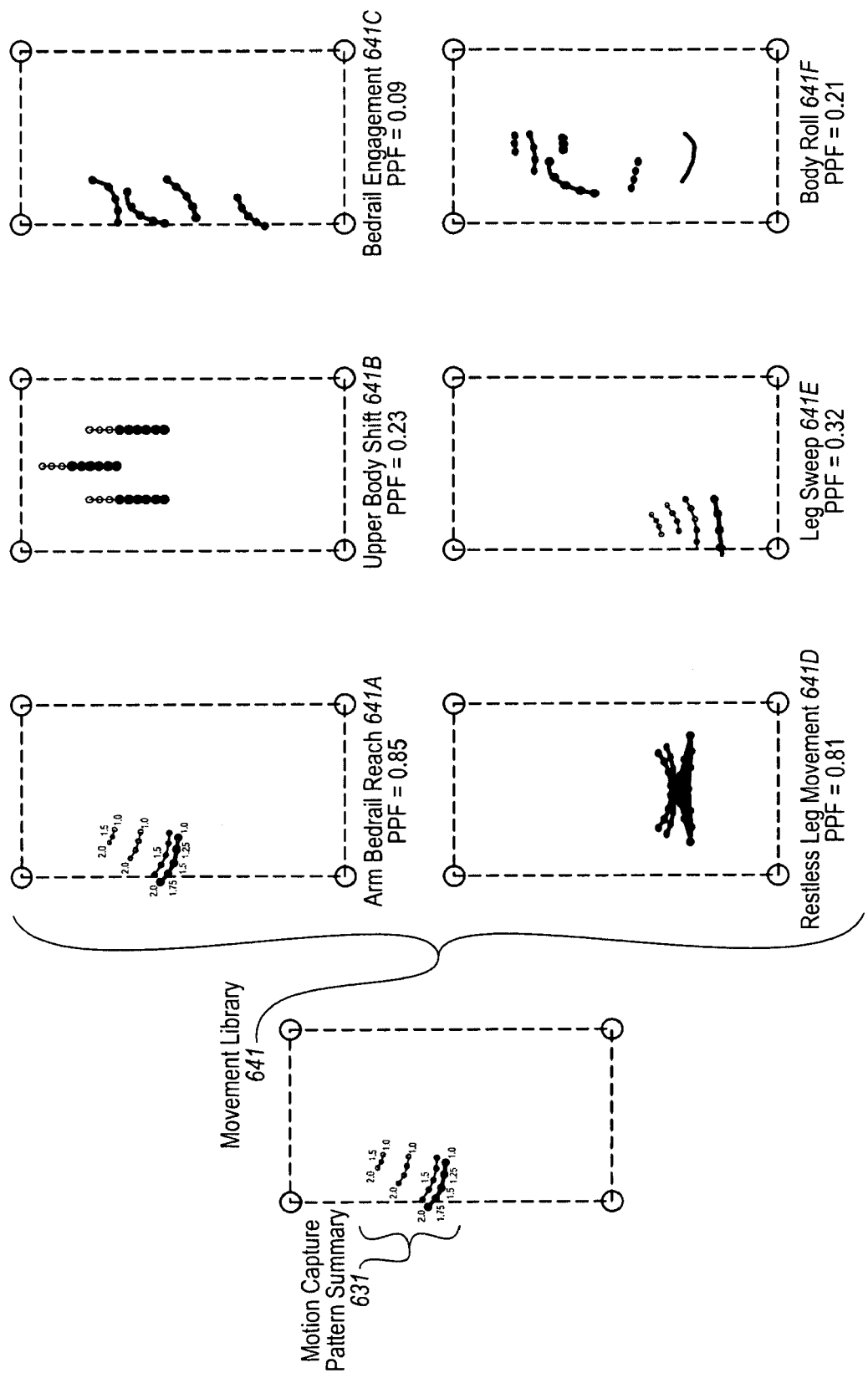
FIG. 6C illustrates comparison of a motion capture pattern summary against a library of movements to indicate the probability of support platform exiting event.

A motion capture pattern summary can be compared against a library of movement pattern data sets that are potentially predictive of platform support exiting for the patient based on known behavior patterns for patients in general and/or the patient specifically. FIG. 6C illustrates motion capture pattern summary 631 relative to various movements in movement library 641. Each movement pattern data set in movement pattern data set library 641 is a movement pattern data set potentially predictive of bed exiting for patient 601. A movement pattern data set potentially predictive of bed (or other support platform) exiting can be based on known behavior patterns for patients in general and/or for patient 601 specifically (e.g., based on a patient profile or other configurable patient related data for patient 601).

In some embodiments, a movement pattern data set library is a general movement pattern data set library equal applicable to a plurality of different patients. In other embodiments, a movement pattern data set library is a custom movement pattern data set library corresponding to a particular patient. For example, movement library 641 can be a custom movement pattern data set library corresponding to patient 601.

Movement pattern data sets in a movement in a movement pattern data set library can be associated with a personal probability factor ("PPF"). A PPF value indicates a probability that a corresponding movement pattern data set is predictive of platform support exiting for a patient. When a movement pattern data set library is generalized, a PPF value can be predictive of platform support existing for patients in general based on generally known patient behavior patterns. When a movement pattern data set library is customized, a PPF value can be predictive of platform support existing for a particular patient based on known behavior patterns for the specific patient.

Thus, PPF values are weighting factors that are based on past (general or specific) patient behavior that correlates with bed exiting. The absence of a particular behavior in connection with bed exiting might lead to an initial PPF value of 0.0. On the other hand, there may be certain known behaviors that correlate so strongly with bed exiting (e.g., vaulting over the bedrail) as to create an actionable event when detected even if the PPF value is low for a given patient. In other words, the PPF value for a given movement for a particular patient is a weighting factor that the computer considers in combination with other weighting factors that may exist for the population as a whole. Accordingly, a combination of personal and non-personal activities and weightings can be used to determine whether there is a high or low probability of support exiting.

Arm bedrail reach 641A illustrates a movement pattern data set having a personal probability factor (PPF) value of 0.85 for a hypothetical patient for an arm bedrail reach.

Upper body shift 641B illustrates a movement pattern data set having a personal probability factor (PPF) value of 0.23 for the hypothetical patient for an upper body shift.

Bedrail engagement 641C illustrates a movement pattern data set having a personal probability factor (PPF) value of 0.09 for the hypothetical patient for bedrail engagement.

Restless leg movement 641D illustrates a movement pattern data set having a personal probability factor (PPF) value of 0.81 for the hypothetical patient for restless leg movement.

Leg sweep 641E illustrates a movement pattern data set having a personal probability factor (PPF) value of 0.32 for the hypothetical for a leg sweep.

Body roll 641F illustrates a movement pattern data set having a personal probability factor (PPF) value of 0.21 for the hypothetical patient for a body roll.

A computer system can compare motion capture pattern summary 631 to each movement pattern data set in movement library 641. If motion capture pattern summary 631 is sufficiently similar to a particular movement pattern data set (e.g., having at least threshold level of commonality), the computer system can detect motion capture pattern summary 631 as an attempted platform support exit. For example, it may be that the computer system compares capture pattern summary 631 to arm bedrail reach 641A.

The computer system can determine that motion capture pattern summary 631 is similar enough to arm bedrail reach 641A to detect with a high degree of probability that patient 601 is reaching for the arm bedrail of bed 603. The computer system can further determine (through general and/or patient specific movement information) that when patient 691 reaches for a bedrail they are likely to be attempting to exit bed 603. In response, the computer system can initiate automated lowering of the support platform of bed 603, contact caregivers, raise bedrails, etc.

Other embodiments include use of a motion capture pattern capture summary (either generalized or customized) in combination with behavioral weighting factors, for example, residing within individual patient profiles. Thus, detected movements can be indicated as more or less likely to be a bed exiting event based on prior patient behavior. Increased behavioral weighting factors can be assigned to motion capture patterns that exhibit a historical correlation to confirmed bed exiting attempts for a patient. For example, if a patient typically attempts to exit a bed by sweeping their leg towards the edge of the bed, the PPF of Leg Sweep 641E can be increased (from 0.32) for the patient or an individual weighting factor for the patient can be added to the PPF of Leg Sweep 641E to reflect this patient behavior. Accordingly, a best fit interpretation of an observed movement pattern can be influenced, at least in part, by historically exhibited bed exiting behaviors for monitored patients.

A configured PPF threshold can be used to alert staff members to a potential bed existing event. For example, when a PPF value for a motion capture pattern equals or exceeds 0.85 staff members can be alerted. When a staff member confirms that a particular motion capture pattern is an attempted bed exiting event (either in response to an alert or through other observation), the PPF for the moving patient can be increased and/or an individual weighting factor can be stored in the patient's profile for the particular motion capture pattern. Thus, subsequently detecting the same motion capture pattern for the patient has an increased likelihood of triggering an alert for the patient (even if it wouldn't necessarily trigger an alert for one or more other patients).

Figure 10:
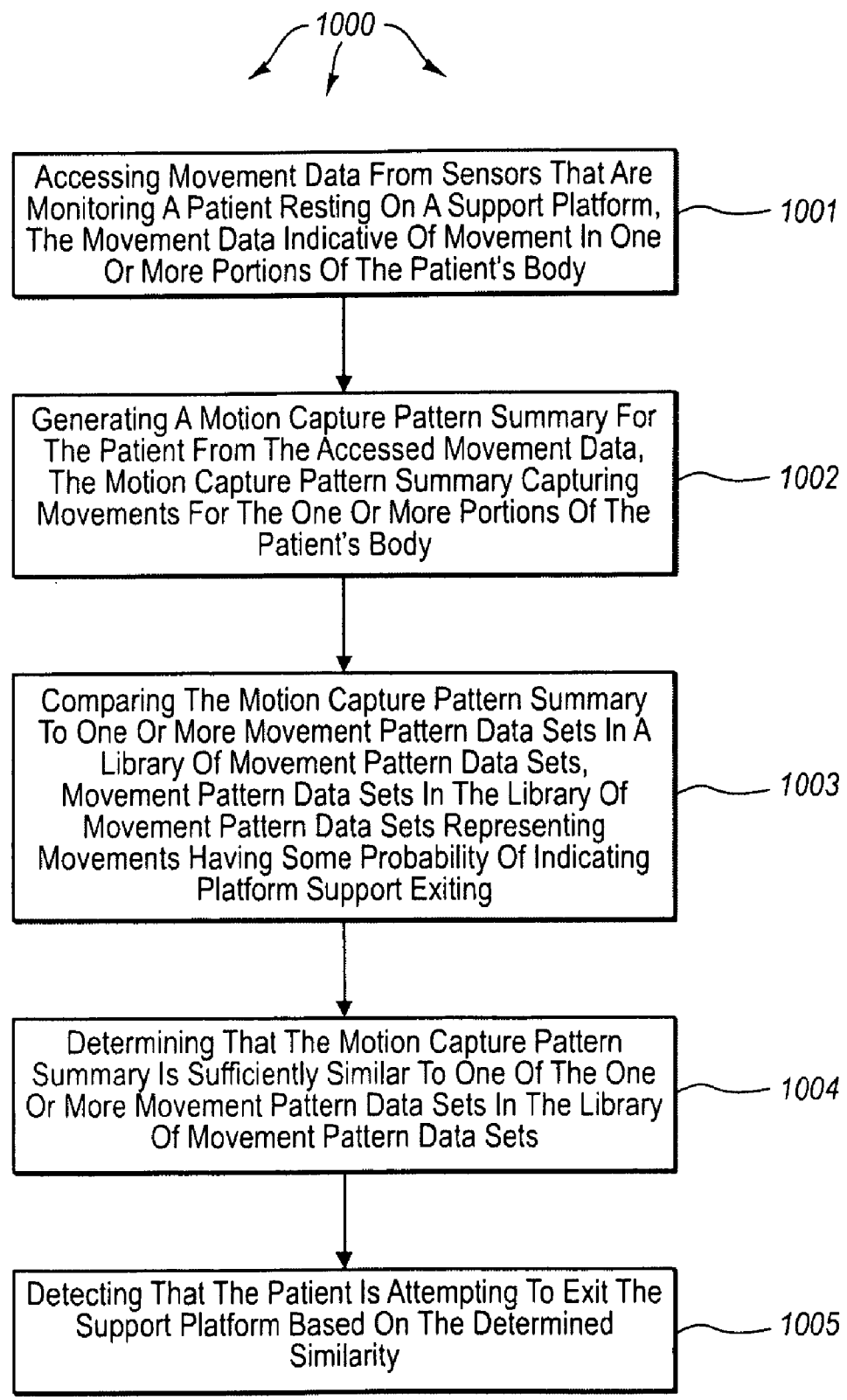
FIG. 10 illustrates a flow chart of an example method for detecting a support exiting event.

FIG. 10 illustrates a flow chart 1000 of an example method for detecting a support exiting event. The method 1000 will be described with respect to the components in operating environment 100 and the movement pattern data and movement pattern data set library in FIGS. 6A-6C.

Method 1000 includes an act of accessing movement data from sensors that are monitoring a patient resting on a support platform, the movement data indicative of movement in one or more portions of the patient's body (act 1001). For example, computer system 104 can access sensors data 122 from sensors 112 that are monitoring patient 118 resting on support platform 103. Sensor data 122 can include data point sets 621 (detected by cameras at patient location 101 of a period time) indicative of movement in the right arm of patient 118.

Method 1000 includes an act of generating a motion capture pattern summary for the patient from the accessed movement data, the motion capture pattern summary capturing movements for the one or more portions of the patient's body (act 1002). For example, computer system 104 can generate motion capture pattern summary 631 from data point set 621. Computer system 104 can digitize and group accessed movement data (e.g., within support platform, 103) into individual clusters of activity as depicted in FIG. 6B. Accordingly, motion capture pattern summary 631 is a digitized representation of captured movements for patient 118's right arm (from T=1.00 to T=2.00).

Method 1000 includes an act of comparing the motion capture pattern summary to one or more movement pattern data sets in a library of movement pattern data sets, movement pattern data sets in the library of movement pattern data sets represent movements having some probability of indicating platform support exiting (act 1003). For example, computer system 104 can compare motion capture pattern summary 631 to movement patterns 641A though 641F in movement library 641. Each of the movement patterns 641A though 641F represent movements (arm bedrail reach, upper body shift, bedrail engagement, restless leg movement, leg sweep, and body roll) that have some probability of indicating that patient 118 is attempting to exit support platform 102.

Method 1000 includes an act of determining that the motion capture pattern summary is sufficiently similar to one of the one or more movement pattern data sets in the library of movement pattern data sets (act 1004). For example, computer system 104 can determined that motion capture pattern summary 631 is sufficiently similar to arm bedrail reach 641A.

Method 1000 includes an act of detecting that the patient is attempting to exit the support platform based on the determined similarity (act 1005). For example, computer system 104 can detect that patient 188 is attempting to reach for the right bedrail of height adjusting bed 102 based on the similarity between motion capture pattern summary 631 and arm bedrail reach 641A. From a combination of general patient behaviors and specific patient behaviors for patient 118, computer system 104 can infer that patient 118 is reaching for the right bedrail for support in an attempt to exit support platform 103. For example, the PPF value of 0.85 plus a patient weighting factor for patient 601 can meet or exceed a configured PFF threshold.

Adjusting Support Platform Height

Figure 7D:
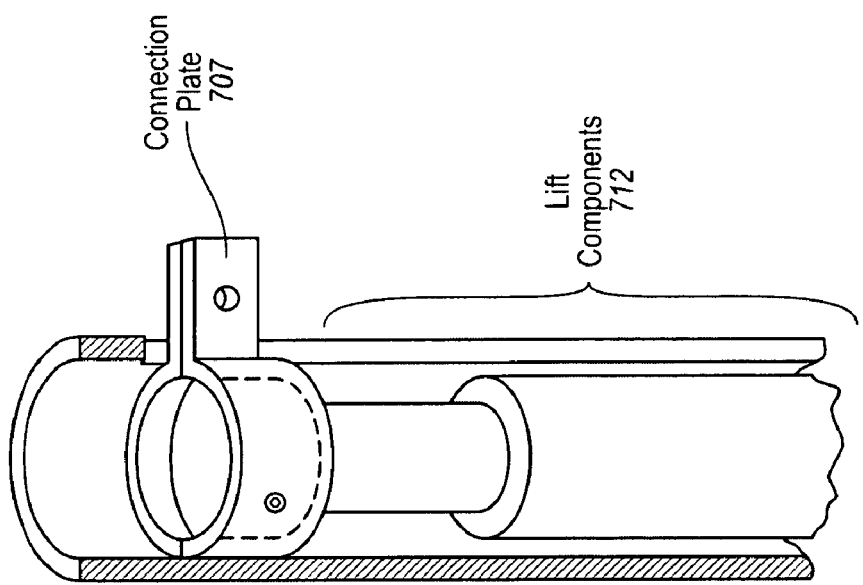
FIG. 7D illustrates an example locking clamp for attaching detaching a support platform to a platform lift.
Figure 7C:
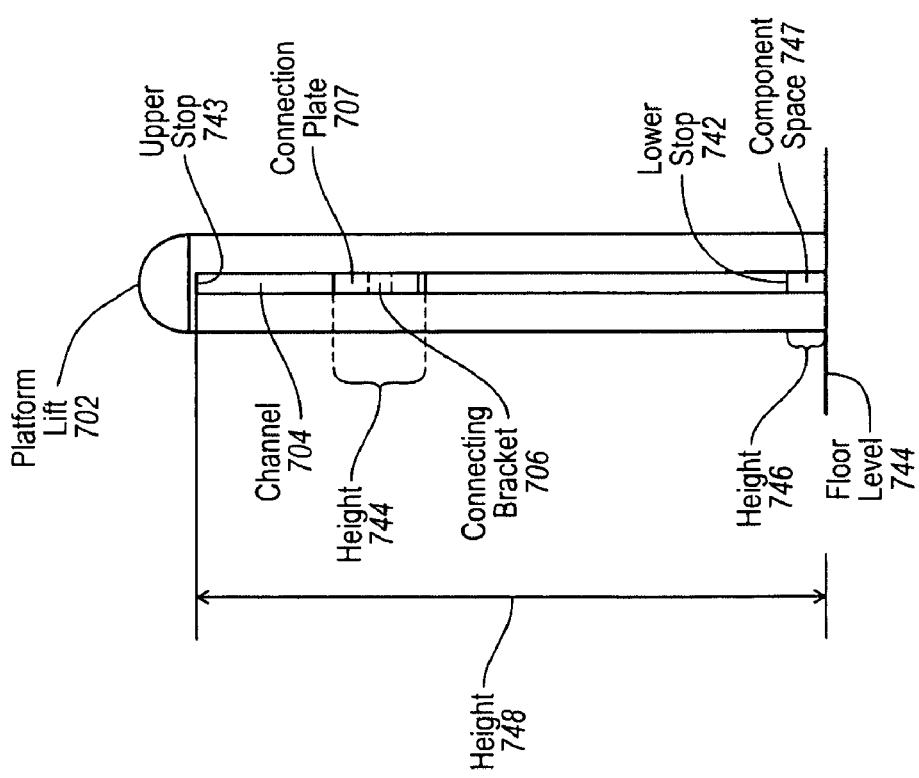
FIG. 7C illustrates an example view of platform lift with a channel allowing vertical movement of a connecting bracket.
Figure 8:
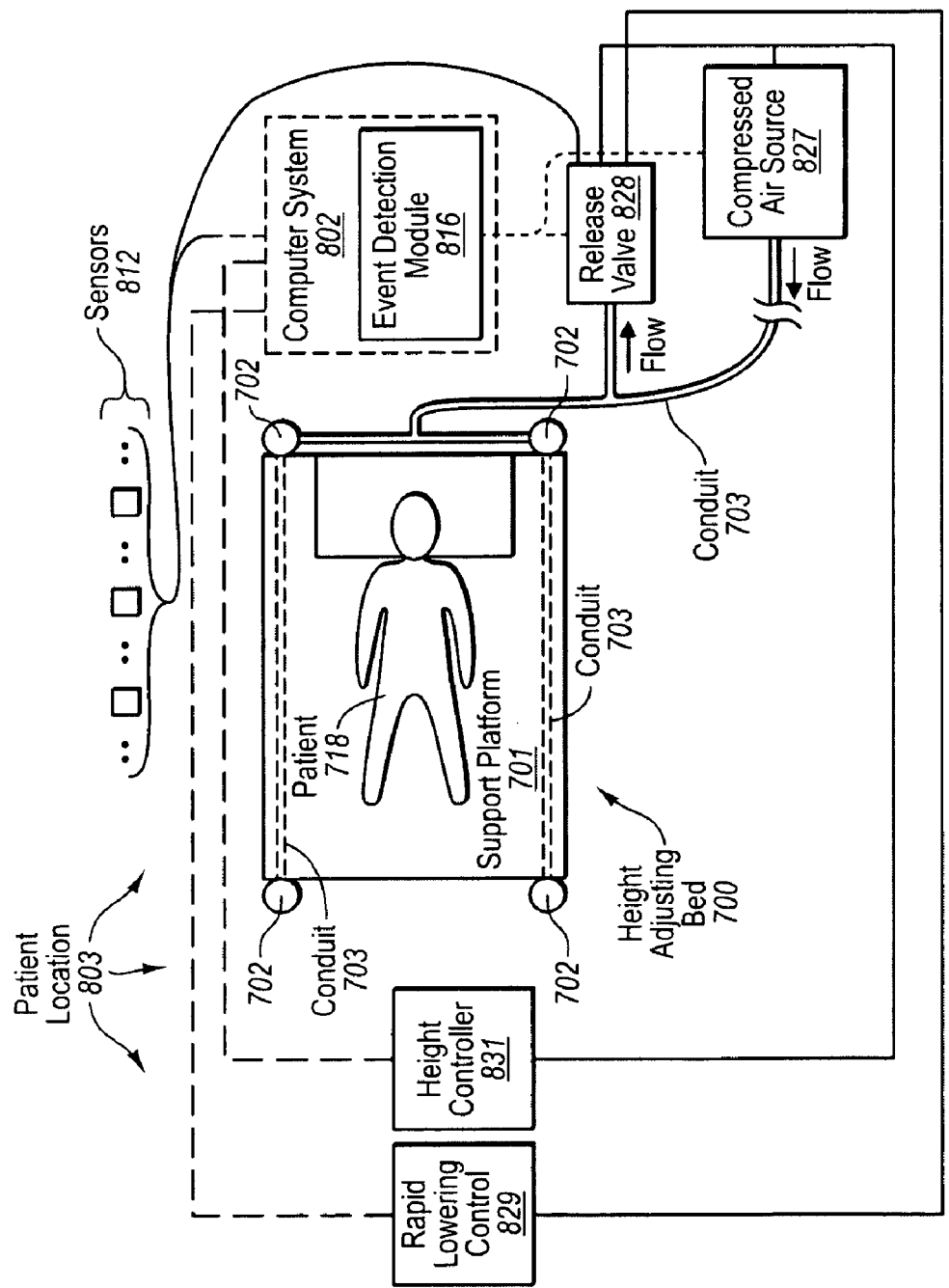
FIG. 8 illustrates a further example of a height adjusting bed in a patient location.

FIGS. 7A through 8 describe various mechanisms that facilitate adjusting (raising and/or lowering) the height of the support platform, including lowering a support platform from a specified height to a lower height to reduce the potential fall distance of a patient in response to detecting that the patient is attempting to exit the patient support platform A support platform can be lowered using a variety of different mechanisms. According to one embodiment of the invention, a height adjusting safety bed includes a support platform configured to support a mattress on top. The support platform interoperates with attachment/detachment mechanisms for attachment to/detachment from platform lifts, such as, for example, at each corner of the support platform. Platform lifts are physically attached to the support platform using the attachment/detachment mechanisms, such as, for example, at each corner of the support platform. Platform lifts can utilize virtually any technology or combination of technologies, such as, for example, mechanical, pneumatic, or hydraulic, to raise or lower the support platform. In some embodiments, a spring assist is used to decelerate lowering of the support platform. A corresponding mattress can also be placed on top of and supported by the support platform. Platform lifts can be selectively activatable in response to signals, such as, for example, from a computer, to raise and/or lower platform lifts.

The components of a height adjusting safety bed can interoperate with each other as well as with a computer system to rapidly and in a controlled manner lower the support platform to essentially floor level. The descent is decelerated in a manner that reduces patient jarring. For example, pneumatic lowering yields a lowering characteristic that is sufficiently rapid yet still decelerates slowly enough to significantly reduce patient jarring when reaching essentially floor level. Patient jarring can be further reduced with a spring assisted descent.

Staff can also use a bed height controller to raise or lower the support platform. In some embodiments, a (manually and/or automatically activatable) rapid lowering control can be activated to rapidly lower the support platform to essentially floor level (e.g., in approximately two seconds or less). Accordingly, when a staff member observes (either directly or via in-room surveillance devices) a support platform exit event, the staff member can activate the rapid lowering control (either remotely from a central station or locally in a patient's room). Further, in-room sensors can detect an exit event and, in response to the detected exit event, the in-room sensors can automatically activate the rapid lowering control. Manually activatable controllers can be integrated with (e.g., externally mounted on) or separately located from the height adjusting safety bed. Separately located controllers can be within a patient's room or even at a nursing station.

In addition to rapid lowering due to unwanted bed exiting (automatic or manually driven), the bed height may be manually raised or lowered by staff to facilitate daily transfers of the patient. The ability to precisely control bed height yields superior clinical outcomes for a range of patient heights and transfer modalities (i.e., bed to stand, walker, wheelchair or scooter).

During lowering, sensors (e.g., infrared, light beam, etc.) can be used to sense any objects beneath the support platform that would prevent lowering the support platform to essentially floor level. Thus, during lowering, the sensors can be used to ensure that no objects are in the path of the descending support platform. If the sensors detect an object that may result in collision, the sensors can initiate an emergency stop of the platform lifts to stop the descent.

In some embodiments, once lowered, a patient is essentially the height of the mattress plus approximately zero to three inches above the floor. This significantly reduces the potential fall distance (e.g., relative to a typical support platform height) for the patient that is attempting to exit the support platform and correspondingly reduces the energy of impact and associated physiological and psychological trauma.

According to one embodiment of the invention, a height adjusting safety bed includes a support platform configured to support a mattress on top. FIG. 7A illustrates an example of a height adjusting bed 700 in a raised configuration. As depicted, height adjusting bed 700 includes support platform 701 and platform lifts 702. Support platform 701 can be of virtually any material with adequate support to mitigate flexion during patient loading. In some embodiments, support platform 701 is made of a metallic mesh with metallic support beams. The base of each platform lift 702 is resting on the floor and thus can be considered to be at floor level 744.

Support platform 701 has corresponding number of connecting brackets 706 that are used to attach support platform 701 to platform lifts 702. Each platform lift 702 has a channel 704 that permits the corresponding connecting bracketing 706 to move vertically within the channel 704. Accordingly, support platform 701 is permitted to move vertically. FIG. 7C illustrates an example view of platform lift 702 with a channel 704 allowing vertical movement of a connecting bracket 706. As depicted, connecting bracket 707 can move vertically to any height between upper stop 741 and lower stop 742.

Lower stop 742 can be height 746 above floor level 744. Lower stop 742 being above floor level allows component space 747 to house lift components used to raise and lower connecting bracket 706. Upper stop 743 can be height 748 above floor level 744. Height 748 can be high enough to permit adjustment of support platform 701 to appropriately accommodate patients of varying heights. For example, upper stop 743 can be approximately 34 inches above floor level. In some embodiments, the height of support platform 701 is initially set to the standard height of a hospital or nursing home bed, such as, for example, 21 inches above floor level 744.

Each platform lift 702 can include one or more internal components that permit a connecting bracket 706 to attach to/detached from lift components of the platform lift 702. In some embodiments, internal components are specifically configured to receive a connecting bracket 706. For example, the upper portion of lift components can include a horizontal plate with a mechanical connecting feature (e.g., a vertical protrusion, hole, etc.) configured to match with a corresponding connecting feature (e.g., a hole, vertical protrusion, etc.) respectively of a connecting bracket. In other embodiments, the components of a platform lift are not specifically configured to receiving a connecting bracket 706.

Height 744 of connecting bracket 706 can be configured to essentially the same as height 746. This permits support platform 701 to be lowered to essentially floor level 744 when height adjusting bed 700 is in it is lowest configuration. For example, FIG. 7B illustrates an example of a height adjusting bed 700 in a lowered configuration. As depicted in FIG. 7B, support platform 701 is essentially at floor level 744.

Each connecting bracket 706 can include one or more attachment/detachment features to attach to/detach from the lift components a platform lift 702. Each attachment/detachment feature can be at least partially incorporated in a connection plate 707 of connecting bracket 706. In some embodiments, each attachment/detachment mechanism is fully integrated into a connection plate 707. For example, it may be that connection plate 707 is a locking clamp for connecting to the lift components of platform lift 702. Accordingly, a connection bracket can include one or more connection plates.

Other external components can also be used to secure a connection plate 707 to lift components of a platform lift 702. For example, an upper portion lift components can include a horizontal plate with a vertical protrusion, wherein the vertical protrusion has a horizontal hole for receiving a safely pin. A connection plate 707 can include a hole configured to accept the vertical protrusion. When connection plate 707 is seated on the horizontal plate, the hole allows the protruding portion to extend above the connection plate 707. A safety pin can then be inserted into the horizontal hole to secure connecting bracket 706 to the lift components.

FIG. 7D depicts an example of an attachment/detachment connection plate 707 for attaching a connecting bracket 706 to and detaching a connecting bracket 706 from the lift components 712 of a platform lift 702. However, virtually any mechanical connecting means, such as, for example, a connecting pin, a screw, a clamp, etc., can be used to attach a connecting bracket 706 to and detach a connecting bracket 706 from the lift components of a platform lift.

Returning now to FIGS. 7A and 7B, conduit 703 runs to each platform lift 702. Conduit 703 can be a pneumatic conduit allowing compressed air to travel to and from each platform lift 702. To raise the support platform 701, conduit 703 can be filled with compressed air. To lower support platform 701, compressed air can be released from conduit 703. Accordingly, embodiments of the invention include a pneumatic lift mechanism to raise and lower support platform 701.

However, platform lifts 702 can utilize virtually any lift component technology, such as, for example, mechanical, pneumatic, or hydraulic, to raise or lower the support platform 701. In some embodiments, a spring assist is used to decelerate lowering of the support platform 701. In embodiments using hydraulic lift mechanisms, conduit 703 can be a hydraulic conduit. In these embodiments, an example pneumatic driven platform lift 702 can be connected to each corner of support platform 701. Each pneumatic driven platform 702 can be connected to conduit 703 and receive compressed air from a common source.

A connection plate 707 connection bracket 706 is attached to internal pneumatic lift components 712 (e.g., variable sized hollow cylinders) within platform lift 702 using any of the previously descried mechanisms. The air pressure (psi) within the internal lift components can be adjusted to correspondingly adjust the height of support platform 701. Pressure can be increased to raise support platform 701 and pressure can be decreased to lower support platform 701.

When the air pressure is increased (flow of compressed air is into the internal lift components), the lift components expand vertically to raise support platform 701. On the other hand, when the air pressure is decreased (flow of compressed air is out of the internal lift components), the internal lift components compress vertically to lower support platform 701. When air pressure is not sufficient to raise support platform (e.g., when essentially all compressed air is released from the internal lift components), support platform 701 is lowered to essentially floor level 744.

Internal lift components can be spring assisted to mitigate patient jarring when a support platform descends. In a raised configuration, a spring expands within platform lift 702. As support platform 701 is lowered, the spring compresses providing resistance to and slowing the descent of platform lift 702. Accordingly, the spring is essentially a shock absorber to lessen any jarring of a patient when support platform 701 is lowered.

It should be understood that lift components 712 can also be hydraulic lift components and conduit 703 can be hydraulic conduit. Accordingly, in these embodiments, support platform 701 can be raised and lowered using fluid instead of compressed air.

Some embodiments of the invention use screw driven platform lifts. A screw driven platform lift 702 can be connected to each corner of support platform 701. Each screw driven platform 702 can be connected to a drive motor. Threaded connection plates can include threads that match threads of a screw within platform lift 702. Threaded connection plates can include a clamp that facilitates attachment to/detachment from threads of in the internal screw.

Thus, the drive motor can rotate threads of the internal screw in one direction (e.g., clockwise) to raise support platform 701 and can rotate threads of the internal screw in another opposite direction (e.g., counter clockwise) to lower support platform 701. Drive motors can be connected to a control line (either digital or analog) and a power (electrical) connection. The control lines control the power applied to and direction of the drive motor so that the drive motor uniformly turns in the same direction at the same speed. In the lowest position, support platform 701 is lowered to essentially floor level 744.

Some embodiments of the invention use chain and gear driven platform lift platforms. A chain and gear driven platform lift 702 can be connected to each corner of support platform 701. Each chain and gear driven platform 702 can be connected to a drive motor 714. A connection plate can be connected to a chain at a connection point (e.g., using a connection pin) within the platform lift 702. Thus, a drive motor can rotate gears in one direction (e.g., counter clockwise) to raise support platform 701 and can rotate gears in another opposite direction (e.g., clockwise) to lower support platform 701. Drive motors can be connected to a control line (either digital or analog), such as, for example, from a computer system and a power (electrical) connection. The control lines control the power applied to and direction of the drive motor so that the drive motor uniformly turns in the same direction at the same speed. In the lowest position, support platform 701 is lowered to essentially floor level 744.

FIG. 7E illustrates an example of a height adjusting bed 700 including a mattress 723 in a raised configuration. FIG. 7F illustrates an example of a height adjusting bed 700 including a mattress 723 in a lowered configuration. In a raised configuration, support platform 701 is height 731 (e.g., 21 inches) above floor level. Thus, a patient resting on mattress 723 would be the sum of height 731 plus mattress height 732 above floor level 744. In a lowered configuration, support platform is height 733 (e.g., zero to three inches) above floor level. Thus, a patient resting on mattress 723 would be the sum of height 733 plus mattress height 732 above floor level 744.

FIG. 8 illustrates an example of a height adjusting bed 700 in a patient location 803. Patient location 803 can be a room in a healthcare facility or patient 818's home. In some embodiments, patient location 803 is configured for patient monitoring, more particularly with respect to monitoring potential support exiting, detecting a position and/or movement of a patient that is predictive of support exiting, obtaining human verification of actual support exiting, and intervening if support exiting is confirmed.

As depicted, height adjusting bed 700 can include pneumatically controlled platform lifts 702. Each pneumatically controlled platform lift 702 is connectable to compressed air source 827 and release valve 828. Each of the pneumatically controlled platform lifts 702 are similarly configured to include lift components 712. Each of the pneumatically controlled platform lifts 702 can also include a spring 708.

Each of the pneumatically controlled platform lifts 702 are connectable to compressed air source 827 and release valve 828 via conduit 703. Compressed air source 827 and release valve 828 can operate to adjust the height of height adjusting bed 700. For example, compressed air source 827 can force compressed air into conduit 103 to raise the height of height adjusting bed 700. On the other hand, release valve 828 can release compressed air from conduit 703 to lower the height of height adjusting bed 700.

Height controller 831 can be used to control compressed air source 827 and release valve 828 so that a staff or family member can adjust the height of height adjusting bed 700. For example, during a controlled exit by patient 818 (e.g., for purposes of a transfer), the height of height adjusting bed 700 can be raised or lowered from a standard height (e.g., 21 inches) to compensate for the height of patient 818. The height can be adjusted to a standing (or walker assisted) position for patient 818. Patient 218 can position himself/herself on the edge of height adjusting bed 700 and then the bed is raised (if patient 818 is taller) or potentially lowered (if patient 818 is shorter) to transition to standing position. Height controller 831 can be connected directly to compressed air source 827 and release valve 828 or can be connected to computer system 802. Height adjusting control 831 can be integrated with (e.g., externally mounted on) or separately located from height adjusting safety bed 700, such as, for example, within a patient's room or even at a nursing station.

Rapid lowering control 829 is a manually activated control that can be used to signal release valve 828 to release any compressed air in conduit 703 in a relatively short period of time (e.g., approximately 2 seconds). Rapid lowering control 829 can be connected directly to release valve 828 or be connected to computer system 802. Rapid lowering control 829 can be integrated with (e.g., externally mounted on) or separately located from height adjusting safety bed 700, such as, for example, within a patient's room or even at a nursing station.

Sensors 812 can include any or a number of different types of sensors, such as, for example, pressure pads, scales, light or IR beam sensors, cameras, acoustic sensors, and induction field sensors, that monitor patient 818 to detect potential bed exiting events. Sensors 812 can be physically attached to height adjusting bed 700 and/or physically located elsewhere at patient location 803 (e.g., wall mounted, floor mounted, ceiling mounted, free standing, etc.) Cameras can be useful in monitoring lateral (i.e., side-to-side) and longitudinal (i.e., head-to-foot) patient movements, although it may also monitor other movements.

Sensors 812 can also includes an audio-video interface that can be used to initiate one-way and/or two-communication with patient 818. The A/V interface can include any combination of known A/V devices, e.g., microphone, speaker, camera and/or video monitor. According to one embodiment, the A/V interface is mounted to a wall or ceiling so as to be seen by patient 818 (e.g., facing the patient's face, such as beyond the foot of the patient's bed). The A/V interface can include a video monitor (e.g., flat panel screen), a camera mounted adjacent to the video monitor (e.g., below), one or more microphones, and one or more speakers. The A/V interface may form part of a computer system 802 that controls the various communication devices located in the patient room.

Thus, sensors 812 can be connected to and interoperate with computer system 802 to determine whether some combination of sensed inputs is indicative of a potential bed exiting event. For example, event detection module 816 can include one or more algorithms (for performing image analysis, video processing, motion analysis, etc.) that process a set of sensed inputs to determine if a potential bed exiting event is occurring.

Alternately, one or more of sensors 812 can be connected directly to release valve 828. The one or more sensors can signal release valve 828 to release any compressed air in conduit 703 in a relatively short period of time.

Accordingly, sensors 812 can be used to implement any of the previously described mechanisms for detecting and responding to a support platform exiting event.

Computer system 802 can be connected to compressed air source 827 and release valve 828 to automatically control the height of height adjusting bed 700 when appropriate. Computer system 802 can also signal release valve 828 to release any compressed air in conduit 703 in a relatively short period of time.

In some embodiments, air pressure levels are used to measure patient body weight. When a patient enters a bed, the increase in measured air pressure may be utilized to predict patient body weight. Patient body weight data may be electronically transferred from the bed lift system to the clinical/quality assurance system for the given medical facility.

In these embodiments, pneumatically driven lift supports house an air pressure gauge within pneumatic sleeves. Calibration of air pressure levels can be converted to weight data on total platform weight (bed+patient). Coordination of weight data with image analysis data can be used to intelligently indicate "weight with patient in bed" and "weight of empty bed."

Similar mechanisms can be used to control the height of a height adjusting bed using hydraulics. When lowering a height adjusting bed, fluid can be recollected in an appropriate reservoir (e.g., at the fluid supply source).

In embodiments that utilize mechanical lift components, height controllers, rapid lowering controls, sensors, and computer systems can be connected to corresponding drive motors.

Thus, embodiments of the invention facilitate manual and/or automated support platform lowering in response to support platform exiting events to reduce the potential fall distance for a patient that is attempting to exit a support platform. For example, a staff member or family member can enter a patient's room (by happenstance, during normal rounds, in response to a notification, etc.) and visual detect that the patient is attempt to exit their bed. In response, the staff member or family member can activate rapid lowering control 829 to signal release valve 828 to rapidly release compressed air (or fluid) in conduit 703 and thus quickly lower the bed's support platform, for example, to essentially floor level.

Alternately, sensors 812 can sense specified inputs indicative of an attempted bed exit, such as, for example, obstruction of an IR or light beam, change in weight of a support platform, etc. In response, sensors 812 can directly signal release valve 828 to rapidly release compressed air (or fluid) in conduit 103 and thus quickly lower the bed's support platform to essentially floor level.

It may also be that event detection module 816 processes a set of sensed inputs to determine that a potential bed exiting event is occurring. In response, computer system 802 can signal release valve 828 to rapidly release compressed air (or fluid) in conduit 703 and thus quickly lower the bed's support platform to essentially floor level. When appropriate, along with or subsequent to lowering support platform 701, computer system 802 can send a notification to a central satiation.

In other embodiments, when set of sensed inputs indicate that a potential bed exiting event is occurring, computer system 802 sends a notification to another network connected computer system subsequent to, in combination with, or for verification of prior to, lowering support platform 701.

In response to the notification (whether it be to verify an attempted bed exit prior to lowering platform support 701 or to indicate that platform support 701 has been lowered), a provider can use in-room surveillance devices (e.g., to activate the A/V interface to patient location 803) to observe/interact with patient 818 and verify the bed exiting event. When a bed exiting event is verified, the provider can initiate further network communication (e.g., to computer system 802) to remotely signal release valve 828 to rapidly release compressed air (or fluid) in conduit 703 and thus quickly lower the bed's support platform to essentially floor level. In either case, a staff member, for example, a responder can be dispatched to patient location 813 for assistance.

In embodiments that utilize mechanical lift components, motors can be activated (by a computer system and/or a human) to rapidly turn a screw drive or chain and gears and thus (potentially rapidly) lower the bed's support platform, for example, to essentially floor level.

Accordingly, in response to a potential bed exiting event, height adjusting bed 700 can be rapidly lowered in a controlled manner to essentially floor level through the actions of an individual, in response to directly sensed inputs, or as a result of data processing activities. The descent can be decelerated in a manner that reduces patient jarring. For example, pneumatic lowering yields a lowering characteristic that is sufficiently rapid yet still decelerates slowly enough to significantly reduce patient jarring when reaching essentially floor level. Patient jarring can be further reduced with a spring assisted descent (e.g., using spring 708) when using any of pneumatic, hydraulic, or mechanical lift components.

In some embodiments, height adjusting bed 700 includes an emergency stopping mechanism and one or more sensors (e.g., infrared, light beam, etc.). The emergency stopping mechanism can stop the descent of support platform 700, even during a rapid descent in response to an attempted bed exit. The stopping mechanism can be a single mechanical mechanism external to platform lifts 702 or can be integrated into each platform lift 702. The one or more sensors are configured to detect objects beneath support platform 701 and signal the emergency stopping mechanism to stop platform descent when an object is detected.

During lowering, sensors can be used to sense any objects (e.g., a patient's foot, leg, etc.) beneath the support platform that would prevent lowering the support platform to essentially floor level and/or cause injury to a patient. Thus, during lowering, the sensors can be used to ensure that no objects are in the path of the descending support platform. If the sensors detect an object that may result in collision, the sensors can initiate an emergency stop of support platform 701 and/or platform lifts 102 to stop the descent.

In some embodiments, once lowered, a patient is essentially the height of the mattress plus approximately zero to three inches above the floor. This significantly reduces the potential fall distance (e.g., relative to a typical support platform height) for the patient that is attempting to exit the support platform.

In some embodiments, a height adjusting bed is connected to a stationary compressed air (or fluid) source of sufficient pressure (e.g., 100+ psi) to raise a height adjusting bed to a desired (e.g., standard) height. For example, hospital and rehabilitation facility rooms can have in-wall compressed air lines (tapped into the building infrastructure) of sufficient pressure to pneumatically lift a height adjusting bed.

In other embodiments, such as, for example, home environments, a height adjusting bed is connected to a moveable compressed air (or fluid) source of sufficient pressure to raise a height adjusting bed to a desired height. For example, a mobile compressor or tank of compressed air can be used to pneumatically lift a height adjusting bed. The mobile compressor or compressed air tank can be physically located in separate room from the patient.

A height adjusting bed can include a mechanical latch that locks the support platform (temporarily) at a current height. The mechanical latch can be engaged to lock the bed at a current height prior to moving in the bed while a patient remains resting on the support platform. The mechanical latch allows the compressed air (or fluid) source to be disconnected with out the support platform lowering. When the bed arrives at its destination, compressed air (or fluid) can be reconnected and the mechanical latch disengaged. Since staff members are likely in close physical proximity during bed movement, there is a reduced chance of an unattended fall. Alternately, a patient can be restrained during transport to avoid a fall.

In some embodiments, a movable cart is connectable to height adjusting bed 700. The moveable cart can be positioned within and attached to each platform lift. Thus, height adjusting bed 700 can be secured to the moveable cart and moved (with or without patients resting on support platform 701) between different physical locations within a facility.

Accordingly, computer system 802 can automatically lower support platform 701 in response to the attempted support exit. Alternately, as previously described, sensors 812 can cause support platform 701 to be rapidly lowered without intervention from computer system 802. In either event, release valve 828 can be sent a signal to release any compressed air (or fluid) from the lift mechanism of support lifts 702. When mechanical lifts are used, a similar signal can be sent to drive motors.

FIGS. 9A-9C depict different configurations of a bed 900 that includes bedrails 941. As depicted, bed 900 includes support platform 901 and platform lifts 902. Mattress 923 rests on support platform 901. Bedrails 941 are also attached to support platform 901. FIG. 9A illustrates an example of bed 900 in a raised configuration with bed rails 941 in a lowered configuration.

As previously described, either alternately to or in combination with lowering a support platform, bedrails of a support platform can be raised to prevent a potential patient fall. FIG. 9B illustrates an example of bed 900 in a raised configuration with bed rails 941 in a raised configuration. FIG. 9C illustrates an example of bed 900 in a lowered configuration with bed rails 941 in a raised configuration.

Computer System Components

Embodiments of the present invention may comprise or utilize a special purpose or general-purpose computer including computer hardware, as discussed in greater detail below. Embodiments within the scope of the present invention also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical storage media and transmission media.

Physical storage media includes RAM, ROM, EEPROM, CD-ROM or other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmission media can include a network and/or data links which can be used to carry or desired program code means in the form of computer-executable instructions or data structures and which can be accessed by a general purpose or special purpose computer. Combinations of the above should also be included within the scope of computer-readable media.

Further, it should be understood, that upon reaching various computer system components, program code means in the form of computer-executable instructions or data structures can be transferred automatically from transmission media to physical storage media. For example, computer-executable instructions or data structures received over a network or data link can be buffered in RAM within a network interface module (e.g., a "NIC"), and then eventually transferred to computer system RAM and/or to less volatile physical storage media at a computer system. Thus, it should be understood that physical storage media can be included in computer system components that also (or even primarily) utilize transmission media.

Computer-executable instructions comprise, for example, instructions and data which cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system and electronic device configurations, including, personal computers, desktop computers, laptop computers, hand-held devices, multi-processor systems, microprocessor-based or programmable consumer electronics, network PCs, minicomputers, mainframe computers, mobile telephones, PDAs, one-way and two-way pagers, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Computer systems can be connected to a network, such as, for example, a Local Area Network ("LAN"), a Wide Area Network ("WAN"), or even the Internet. Thus, the various components can receive data from and send data to each other, as well as other components connected to the network. Networked computer systems may themselves constitute a "computer system" for purposes of this disclosure.

Networks facilitating communication between computer systems and other electronic devices can utilize any of a wide range of (potentially interoperating) protocols including, but not limited to, the IEEE 802 suite of wireless protocols, Radio Frequency Identification ("RFID") protocols, infrared protocols, cellular protocols, one-way and two-way wireless paging protocols, Global Positioning System ("GPS") protocols, wired and wireless broadband protocols, ultra-wideband "mesh" protocols, etc. Accordingly, computer systems and other devices can create message related data and exchange message related data (e.g., Internet Protocol ("IP") datagrams and other higher layer protocols that utilize IP datagrams, such as, Transmission Control Protocol ("TCP"), Remote Desktop Protocol ("RDP"), Hypertext Transfer Protocol ("HTTP"), Simple Mail Transfer Protocol ("SMTP"), etc.) over the network.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. At a computer system, a method for detecting a support platform exiting event, the method comprising:

accessing movement data from sensors that are monitoring a patient resting on a support platform, the movement data indicative of movement in one or more portions of the patient's body;

generating a motion capture pattern summary for the patient from the accessed movement data, the motion capture pattern summary capturing movements for the one or more portions of the patient's body;

comparing the motion capture pattern summary to one or more movement pattern data sets in a library of movement pattern data sets, the one or more movement pattern data sets in the library of movement pattern data sets being representative of movements having some probability of indicating platform support exiting;

determining that the motion capture pattern summary is sufficiently similar to one of the one or more movement pattern data sets in the library of movement pattern data sets; and detecting that the patient is attempting to exit the support platform based on the determined similarity by:

accessing a general probability factor corresponding to the one or more movement pattern data sets, the general probability factor generally indicative of the probability of the detected movement corresponding to a support platform exiting event;

accessing a behavioral weighting factor for the patient, the value of the behavioral weighting factor based on prior detections of movement pattern data sets confirmed as support platform exiting attempts by the patient;

combining the probability factor and the behavioral weighting factor into a patient specific probability factor; and determining that the patient specified probability factor satisfies a configured probability threshold indicative of a support platform exiting event.

2. The method as recited in claim 1, wherein accessing data from sensors that are monitoring a patient resting on a support platform comprises accessing video data from one or more cameras that are monitoring the patient resting on the support platform.

3. The method as recited in claim 1, wherein accessing data from sensors that are monitoring a patient resting on a support platform comprises accessing data from a light beam matrix.

4. The method as recited in claim 1, wherein accessing data from sensors that are monitoring a patient resting on a support platform comprises accessing data from an RFID grid system.

5. The method as recited in claim 1, wherein generating a motion capture pattern summary for the patient from the accessed movement data comprises digitizing the accessed movement data.

6. The method as recited in claim 1, wherein generating a motion capture pattern summary for the patient from the accessed movement data comprises grouping the accessed movement data into individual clusters of activity.

7. The method as recited in claim 1, wherein comparing the motion capture pattern summary to one or more movement pattern data sets in a library of movement pattern data sets comprises an act comparing the motion capture pattern summary to one or more movement pattern data sets generally indicative of platform support exiting.

8. The method as recited in claim 1, wherein comparing the motion capture pattern summary to one or more movement pattern data sets in a library of movement pattern data sets comprises an act comparing the motion capture pattern summary to one or more movement pattern data sets specifically indicative of platform support exiting by the patient.

9. The method as recited in claim 1, wherein determining that the motion capture pattern summary is sufficiently similar to one of the one or more movement pattern data sets in the library of movement pattern data sets comprises an act of determining that the motion capture pattern summary is sufficiently similar to one or more of: a bed rail reach, an upper body shift, a bedrail engagement, restless leg movement, a leg sweep, and a body roll.

10. The method as recited in claim 1, wherein detecting that the patient is attempting to exit the support platform based on the determined similarity comprises:

accessing the patient specific probability factor corresponding to the one or more detected movement pattern data sets; and determining that the accessed probability factor satisfies a configured probability threshold indicative of a bed exiting event.

11. The method as recited in claim 1, wherein detecting that the patient is attempting to exit the support platform based on the determined similarity comprises:

determining that the patient specified probability factor satisfies a configured probability threshold indicative of a bed exiting event.

12. The method as recited in claim 1, further comprising lowering the height of the support platform to reduce the potential fall distance of the patient in response to detecting that the patient is attempting to exit the support platform.

13. The method as recited in claim 12, wherein lowering the height of the support platform from the specified height to a lower height to reduce the potential fall distance of the patient comprises lowering the support platform of a bed, wherein the bed further comprises:

a plurality of platform lifts, each platform lift including:

a lift component configured to raise and lower in response to an appropriate signal, including rapidly lowering to essentially floor level in response to a signal indicating a potential bed exiting event;

a channel permitting external components attached to the lift component to raise and lower with the lift component; and a corresponding plurality of connecting brackets affixed to the support platform, each connecting bracket including a connection plate, each connection plate extending into a channel of a platform lift and attached to a lift component of a corresponding platform lift; and wherein the support platform is lowered by appropriately signaling each of the plurality of lift platforms to lower the support platform.

14. The method as recited in claim 13, further comprising raising bedrails of the support platform to attempt to prevent the patient from exiting the support platform in response to detecting that the patient is attempting to exit the support platform.

15. The method as recited in claim 1, further comprising electronically notifying a care giver that the support platform is being and/or was lowered.

16. A computer program product for use at a computer system, the computer program product for implementing a method for detecting a support platform exiting event, the computer program product comprising one or more computer-readable medium having stored thereon computer-executable instructions that, when executed at a processor, cause the computer system to perform the following:

access movement data from sensors that are monitoring a patient resting on a support platform, the movement data indicative of movement in one or more portions of the patient's body;

generate a motion capture pattern summary for the patient from the accessed movement data, the motion capture pattern summary capturing movements for the one or more portions of the patient's body;

compare the motion capture pattern summary to one or more movement pattern data sets in a library of movement pattern data sets, the one or more movement pattern data sets in the library of movement pattern data sets being representative of movements having some probability of indicating platform support exiting;

determine that the motion capture pattern summary is sufficiently similar to one of the one or more movement pattern data sets in the library of movement pattern data sets; and detect that the patient is attempting to exit the support platform based on the determined similarity by:

accessing a general probability factor corresponding to the one or more movement pattern data sets, the general probability factor generally indicative of the probability of the detected movement corresponding to a support platform exiting event;

accessing a behavioral weighting factor for the patient, the value of the behavioral weighting factor based on prior detections of movement pattern data sets confirmed as support platform exiting attempts by the patient;

combining the probability factor and the behavioral weighting factor into a patient specific probability factor; and determining that the patient specified probability factor satisfies a configured probability threshold indicative of a support platform exiting event.

17. The computer program product as recited in claim 16, wherein computer-executable instructions that, when executed at a processor, cause the computer system to detect that the patient is attempting to exit the support platform based on the determined similarity comprise computer-executable instructions that, when executed at a processor, cause the computer system to:

access the patient specific probability factor corresponding to the one or more movement pattern data sets; and determine that the accessed probability factor satisfies a configured probability threshold indicative of a bed exiting event.

18. The computer program product as recited in claim 16, wherein computer-executable instructions that, when executed at a processor, cause the computer system to detect that the patient is attempting to exit the support platform based on the determined similarity comprise computer-executable instructions that, when executed at a processor, cause the computer system to:

determine that the patient specified probability factor satisfies a configured probability threshold indicative of a bed exiting event.

19. At a computer system, a method for responding to a support platform exiting event, the method comprising:

accessing patient movement data from sensors that are monitoring a patient resting on a support platform, the patient movement data indicative of movement in one or more portions of the patient's body, the support platform being a specified height above floor level;

determining that the accessed patient movement data is sufficiently similar to one or more movement pattern data sets in a library of movement pattern data sets, the one or more movement pattern data sets in the library of movement pattern data sets being indicative of movements having an increased probability of platform support exiting, wherein determining that the accessed patient movement data and is sufficiently similar to one or more movement pattern data set comprises:

accessing a general probability factor corresponding to the one or more movement pattern data sets, the general probability factor generally indicative of the probability of the detected movement corresponding to a support platform exiting event;

accessing a behavioral weighting factor for the patient, the value of the behavioral weighting factor based on prior detections of movement pattern data sets confirmed as support platform exiting attempts by the patient;

combining the probability factor and the behavioral weighting factor into a patient specific probability factor; and determining that the patient specified probability factor satisfies a configured probability threshold indicative of a support platform exiting event; and lowering the height of the support platform from the specified height to a lower height to reduce the potential fall distance of the patient in response to determining that the access patient movement data is sufficiently similar to the one or more movement pattern data sets in the library of movement pattern data sets.

20. The method as recited in claim 19, wherein accessing patient movement data from sensors that are monitoring a patient resting on a support platform comprises access patient movement data from cameras that are monitoring the patient.

21. The method as recited in claim 19, wherein accessing patient movement data from sensors that are monitoring a patient resting on a support platform comprises accessing patient movement data from an ultrasound grid system.

22. The method as recited in claim 19, wherein determining that the accessed patient movement data and is sufficiently similar to one or more movement pattern data set comprises:

digitizing the accessed movement data;

grouping the digitized accessed movement data into individual clusters of activity; and comparing the clusters of activity to the or more movement pattern data sets.

23. The method as recited in claim 19, wherein determining that the accessed patient movement data and is sufficiently similar to one or more movement pattern data set comprises:

accessing the patient specific probability factor corresponding to one of the one or more movement pattern data sets; and determining that the accessed probability factor satisfies a configured probability threshold indicative of a bed exiting event.

24. The method as recited in claim 19, wherein determining that the accessed patient movement data and is sufficiently similar to one or more movement pattern data set comprises:

determining that the patient specified probability factor satisfies a configured probability threshold indicative of a bed exiting event.

25. The method as recited in claim 19, wherein lowering the height of the support platform from the specified height to a lower height to reduce the potential fall distance of the patient comprises signaling a release valve to release compressed air from one or more pneumatic platform support lifts supporting the platform support at the specified height.

26. The method as recited in claim 19, wherein lowering the height of the support platform from the specified height to a lower height to reduce the potential fall distance of the patient comprises signaling a release valve to release fluid from one or more hydraulic platform support lifts supporting the platform support at the specified height.

27. The method as recited in claim 19, wherein lowering the height of the support platform from the specified height to a lower height to reduce the potential fall distance of the patient comprises signaling a driver motor to lower a platform support lift selected from among: a screw driven platform support and a chain driver platform support lift.

28. The method as recited in claim 19, wherein lowering the height of the support platform from the specified height to a lower height to reduce the potential fall distance of the patient comprises lowering the height of the support platform form the specified height to between zero to three inches above floor level in two seconds or less.

29. At a computer system, a method for responding to a patient attempting to exit a bed in a healthcare facility, the bed including:
  a support platform, the support platform being a specified height above floor level;
  a plurality of platform lifts, each platform lift including:
    a pneumatic lift component configured to raise and lower in response to changes in compressed air supplied to the platform lift, including rapidly lowering to essentially floor level in response to a signal indicating a potential bed exiting event;
    a spring configured to lower the rate of deceleration of the corresponding lift component when the lift component is rapidly lowered to essentially floor level; and
    a channel permitting external components attached to the lift component to raise and lower with the lift component;
  a corresponding plurality of connecting brackets affixed to the support platform, each connecting bracket including a connection plate, each connection plate extending into a channel of a platform lift and attached to a pneumatic lift component of a corresponding platform lift; and
  a conduit connected to each of the platform lifts, the conduit for transferring compressed air at each platform lift used to regulate the height each of the plurality of lift components respectively; and
  a release valve couple to the conduit for releasing compressed air from the pneumatic lift components, the method comprising:
  accessing movement data from sensors that are monitoring a patient resting on a support platform, the movement data indicative of movement in one or more portions of the patient's body;
  generating a motion capture pattern summary for the patient from the accessed movement data, the motion capture pattern summary capturing movements for the one or more portions of the patient's body;
  comparing the motion capture pattern summary to one or more movement pattern data sets in a library of movement pattern data sets, the one or more movement pattern data sets in the library of movement pattern data sets being indicative of movements having an increased probability of platform support exiting;
  determining that the motion capture pattern summary is sufficiently similar to one of the one or more movement pattern data sets in the library of movement pattern data sets by:
    accessing a general probability factor corresponding to the one or more movement pattern data sets, the general probability factor generally indicative of the probability of the detected movement corresponding to a bed exiting event;
    accessing a behavioral weighting factor for the patient, the value of the behavioral weighting factor based on prior detections of movement pattern data sets confirmed as bed exiting attempts by the patient;
    combining the probability factor and the behavioral weighting factor into a patient specific probability factor; and
    determining that the patient specified probability factor satisfies a configured probability threshold indicative of a bed exiting event; and
  signaling the release valve to release compressed air from the pneumatic lift components to lower the height of the support platform of the bed from the specified height to the a lower height to reduce the potential fall distance of the patient.

30. The method as recited in claim 29, wherein generating a motion capture pattern summary for the patient from the accessed movement data comprises:
  digitizing the accessed movement data; and
  grouping the digitized accessed movement data into individual clusters of activity.

* * * * *

UNITED STATES PATENT AND TRADEMARK OFFICE
CERTIFICATE OF CORRECTION

PATENT NO.       : 7,987,069 B2
APPLICATION NO.  : 12/268728
DATED            : July 26, 2011
INVENTOR(S)      : Rodgers et al.

It is certified that error appears in the above-identified patent and that said Letters Patent is hereby corrected as shown below:

Title Page 2, Item 56, References Cited, OTHER PUBLICATIONS, Right Hand Column
Change the reference "Chang, et al., Pervasive Observation Medicine: The Application of RFID to Improve Patent Safety in Observation Unit of Hospital Emergency Department, 2005." to --Chang, et al., Pervasive Observation Medicine: The Application of RFID to Improve Patient Safety in Observation Unit of Hospital Emergency Department, 2005.--

Drawings
Sheet 2, replace Figure 2 with the figure depicted below, wherein "Video Stream 316A" has been changed to --Video Stream 216A--

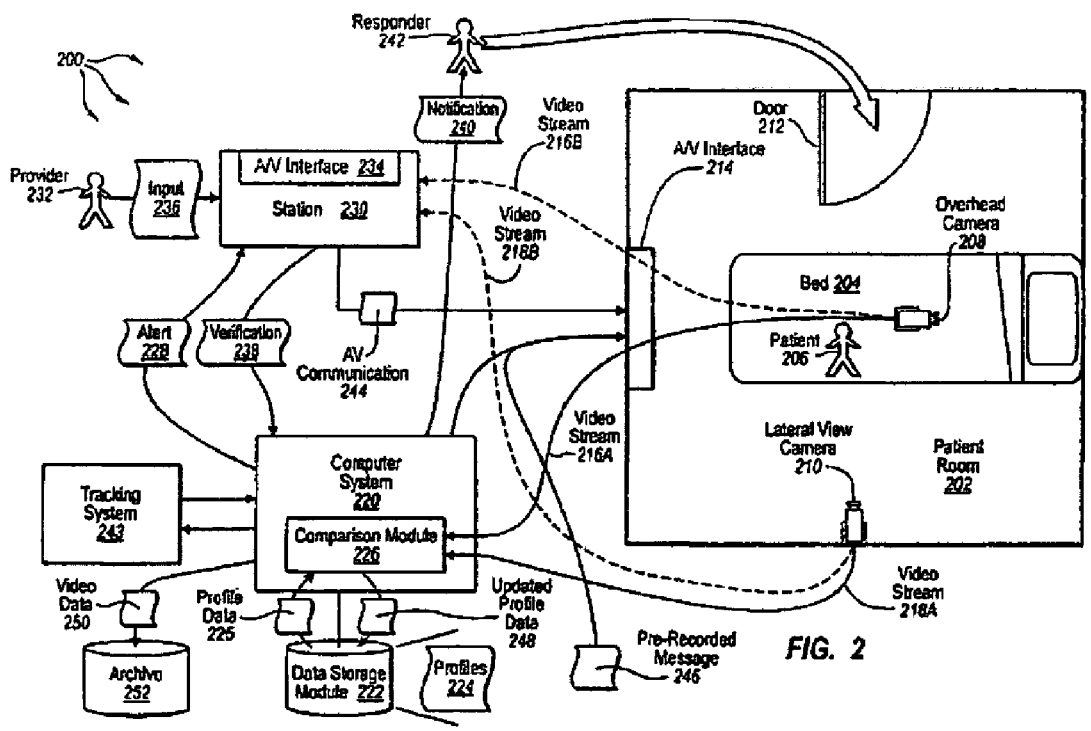

Signed and Sealed this
Eleventh Day of October, 2011

David J. Kappos
Director of the United States Patent and Trademark Office

CERTIFICATE OF CORRECTION (continued)
U.S. Pat. No. 7,987,069 B2

Sheet 3, replace Figure 3A with the figure depicted below, wherein "Flat Panel Video Monitor 316" has been changed to --Flat Panel Video Monitor 314--

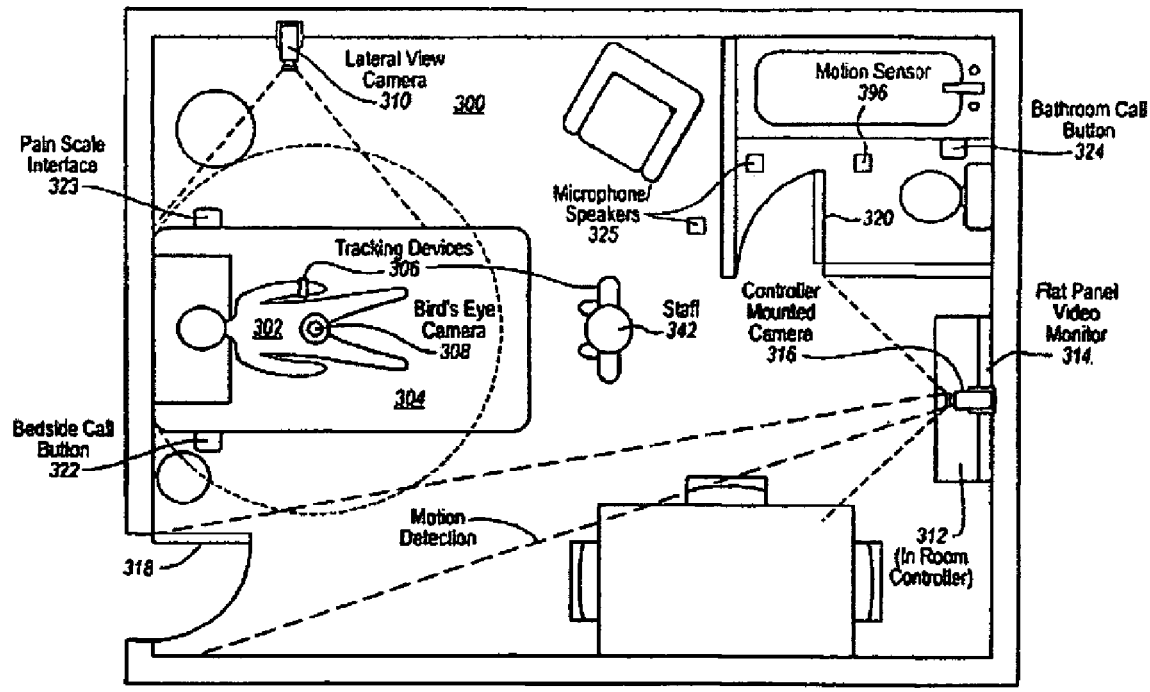

FIG. 3A

CERTIFICATE OF CORRECTION (continued)
U.S. Pat. No. 7,987,069 B2

Sheet 4, replace Figure 3B with the figure depicted below, wherein a door has been labeled --311-- and the "Patient Room 300" has been changed to --Patient Room 350--

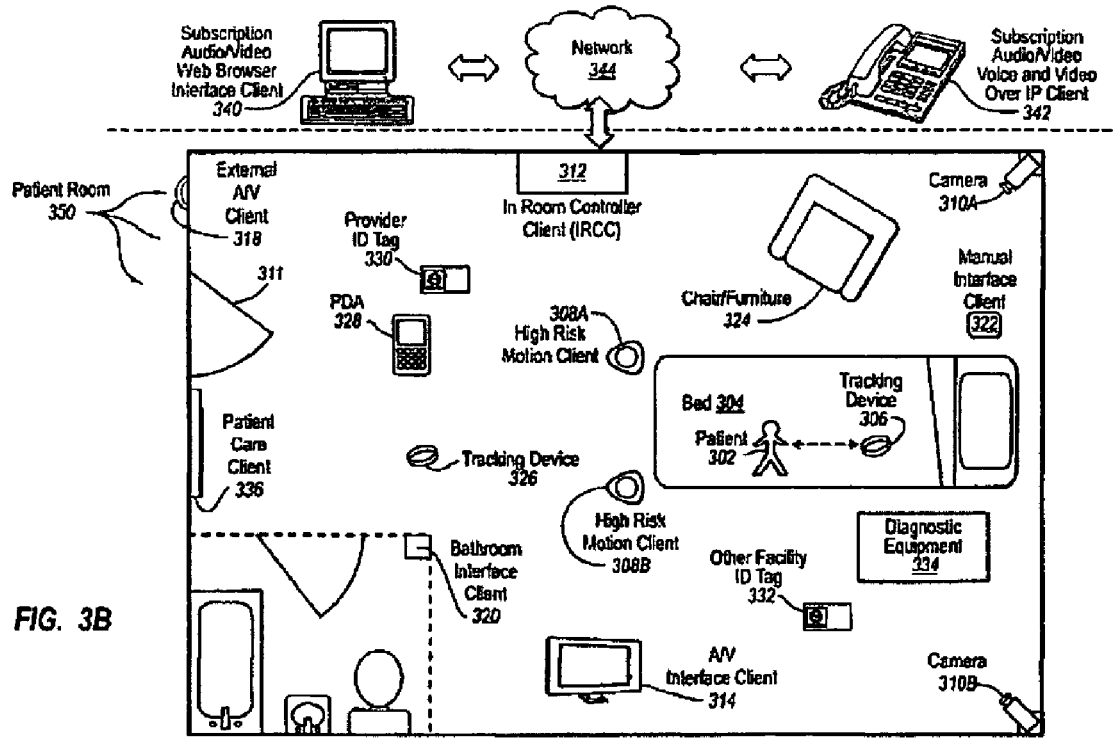

FIG. 3B

Sheet 14, replace Figure 8 with the figure depicted below, wherein "Patient 718" has been changed to --Patient 818--

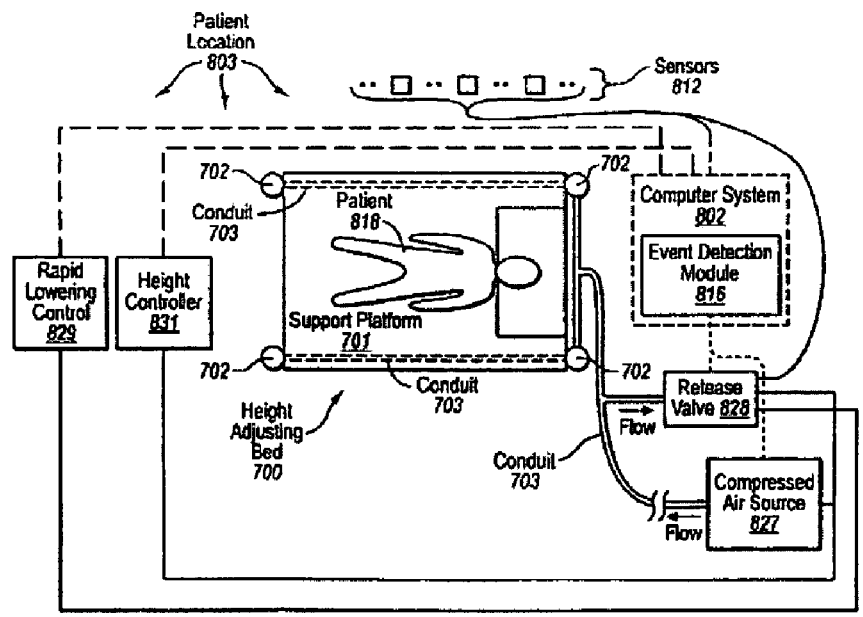

FIG. 8

CERTIFICATE OF CORRECTION (continued)
U.S. Pat. No. 7,987,069 B2

Column 1
Line 15, change "entirety" to --entirety.--
Line 29, change "circumstance" to --circumstances--

Column 3
Line 34, after "attaching" insert --or--

Column 4
Line 46, change "other, hand" to --other hand,--
Line 46, change "physical" to --physically--
Lines 48-49, change "computer system 101" to --computer system 104--

Column 5
Line 23, change "at" to --an--
Line 56, change "computer system 103" to --computer system 104--
Line 62, before "health care provider" insert --a--
Line 65, change "attempt" to --attempting--

Column 6
Line 11, change "provides" to --providers--
Line 12, change "physical" to --physically--
Line 12, change "access the health or" to --assess the health of--
Line 33, change "than" to --when--
Line 36, change "position some higher" to --position to some higher--
Line 44, change "variety or different" to --variety of different--
Line 57, change "facilities" to --facilitates--

Column 7
Lines 10-11, change "two-communication" to --two-way communication--
Line 48, change "Computer system 320" to --Computer system 220--
Line 49, change "such an in" to --such as an in--

Column 8
Line 4, change "sends" to --send--
Line 43, change "lower" to --lowering--

Column 9
Line 14, change "patient 306" to --patient 206--
Line 65, change "patients" to --patient's--

Column 10
Line 22, change "person's" to --persons--
Line 24, change "staff 3 32" to --staff 342--
Line 44, change "staff 3 32" to --staff 342--
Line 67, change "bed 204" to --bed 304--

Column 11
Line 12, change "cameras 308, 310" to --cameras 310A, 310B--
Line 24, change "bed 204" to --bed 304--
Line 29, change "bed 204" to --bed 304--

Column 12
Line 3, change "direct" to --directly--
Line 17, change "interface client 330" to --interface client 340--
Line 23, change "depict" to --depicts--
Line 27, change "demine" to --determine--
Line 37, change "470" to --466--
Line 38, change "466" to --470--
Line 51, change "up upward" to --of upward--

Column 14
Line 48, change "such as," to --such as--
Line 57, change "base" to --based--

Column 15
Line 67, change "act 1002" to --act 1102--

Column 16
Line 45, change "similarly" to --similar--

Column 17
Line 3, change "position some higher" to --position to some higher--
Line 5, change "similarly" to --similar--
Lines 21-22, bold "308", "310", and "316"
Line 29, change "systems" to --system--

Column 18
Line 18, change "arm 611 is moved to position 602" to --arm 602 is moved to position 611--
Line 23, change "systems" to --system--
Line 26, change "can generated" to --can be generated--
Line 37, change "combining" to --combined--
Line 45, change "Movement pattern 632C" to --Movement pattern 631C--
Line 47, change "Movement pattern 632D" to --Movement pattern 631D--

Column 19
Line 5, change "equal" to -- equally--
Line 12, remove the second instance of [in a movement]
Line 18, change "existing" to --exiting--
Line 21, change "existing" to --exiting--
Line 60, change "least threshold" to --least a threshold--

CERTIFICATE OF CORRECTION (continued)
U.S. Pat. No. 7,987,069 B2

Column 20
Line 3, change "patient 691" to --patient 601--
Line 26, change "existing" to --exiting--
Line 47, change "sensors" to --sensor--
Line 60, change "support platform, 103" to --support platform 103--

Column 21
Line 15, change "can determined" to --can be determined--
Line 21, change "patient 188" to --patient 118--

Column 22
Line 51, change "has corresponding" to --has a corresponding--
Line 59, change "connecting bracket 707" to --connecting bracket 706--
Line 60, change "upper stop 741" to --upper stop 743--

Column 23
Line 8, change "detached" to --detach--
Line 17, change "receiving" to --receive--
Line 19, change "essentially" to --be essentially--
Line 21, change "is in it is" to --is in its--
Line 37, change "components" to --component--
Line 39, change "safely" to --safety--

Column 24
Line 6, change "707 connection" to --707 of connection--
Line 9, change "descried" to --described--
Line 33, change "can be hydrau-" to --can be a hydrau- --
Line 44, change "threads of in" to --threads in--

Column 25
Line 39, change "conduit 103" to --conduit 703--
Line 51, change "Patient 218" to --Patient 818--

Column 26
Line 16, change "includes" to --include--
Line 18, change "two-communication" to --two-way communication--

Column 27
Line 11, change "visual" to --visually--
Line 12, change "attempt" to --attempting--
Line 23, change "conduit 103" to --conduit 703--
Line 37, change "of prior to" to --prior to--
Line 50, change "patient location 813" to --patient location 803--

Column 28
Line 21, change "platform lifts 102" to --platform lifts 702--
Line 41, after "located in" insert --a--
Line 49, change "with out" to --without--

Column 29
Line 52, change "carry or desired" to --carry desired--

Column 34
Line 5, change "data and is" to --data is--
Line 38, change "data and is" to --data is--
Line 55, change "data and is" to --data is--
Line 55, change "data and is" to --data is--

Column 35
Line 16, change "form" to --from--
Line 47, change "height each" to --height of each--
Line 49, change "couple" to --couipled--

Column 36
Line 40, change "height to the a lower" to --height to a lower--